(12) United States Patent
Booher et al.

(10) Patent No.: US 6,558,918 B1
(45) Date of Patent: *May 6, 2003

(54) NUCLEIC ACID THAT ENCODE A CELL GROWTH REGULATORY PROTEIN

(75) Inventors: Robert N. Booher, San Francisco, CA (US); Ali Fattaey, San Francisco, CA (US)

(73) Assignee: Onyx Pharmaceuticals, Inc., Richmond, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/951,034

(22) Filed: Oct. 15, 1997

Related U.S. Application Data
(60) Provisional application No. 60/031,266, filed on Nov. 15, 1996.

(51) Int. Cl.[7] .................. C12N 15/52; C12N 15/12; C12N 5/10; C12N 15/63
(52) U.S. Cl. ............... 435/69.1; 435/320.1; 435/325; 435/183; 536/23.5; 536/23.2; 536/24.3
(58) Field of Search .................. 514/44; 536/23.5, 536/23.2, 23.51; 435/320.1, 325, 252.3, 254.11, 194, 183, 69.1

(56) References Cited

U.S. PATENT DOCUMENTS
5,744,349 A * 4/1998 Piwnica-Worms ....... 435/252.3

FOREIGN PATENT DOCUMENTS
WO  WO 97/32473  9/1997

OTHER PUBLICATIONS

Lewin, Science, 237, 1570, 1987.*
Reeck, Cell, 50, 667, 1987.*
George et al., Macromolecular Sequencing and Synthesis, 127–149, 1988, Alan R. Liss, Inc.*
Tassan, J. Cell Biol. 127, 467–478, 1994.*
Mueller et al., "Myt1: A Membrane–Associated Inhibitory Kinase That Phosphorylates Cdc2 on Both Threonine–14 and Tyrosine–15", SCIENCE, vol. 270, Oct. 6, 1995 (pp. 86–90).
Mills et al. "Interleukin 2–induced Tyrosine Phosphorylation" The Journal of Biological Chemistry, vol. 265 No. 6, pp 3561–3567, 1990.
Liu et al. "The Human Myt1 Kinase Preferentially Phosphorylates Cdc2 . . . " Molecular and Cell Biology, vol. 17 No. 2, pp 571–583, 1997.
Fessler et al. "Cell Cycle Regulation of the p34cdc2 Inhibitory Kinases" Molecular Biology of the Cell, vol. 5, pp 989–1001, 9/94.

* cited by examiner

*Primary Examiner*—Michael Pak
(74) *Attorney, Agent, or Firm*—Gregory Giotta

(57) ABSTRACT

Compositions of matter consisting of a family of related nucleic acid sequences that encode proteins, termed Cell Growth Regulatory Proteins, that phosphorylate cell cycle targets, and methods of using the nucleotide sequences and the proteins encoded thereby, to diagnose and/or treat disease where the Cell Growth Regulatory Proteins have an apparent molecular weight of about 54.6 kdaltons.

11 Claims, 2 Drawing Sheets

Human Myt1 Transmembrane Region pCMV-HA:MYT1 Constructs

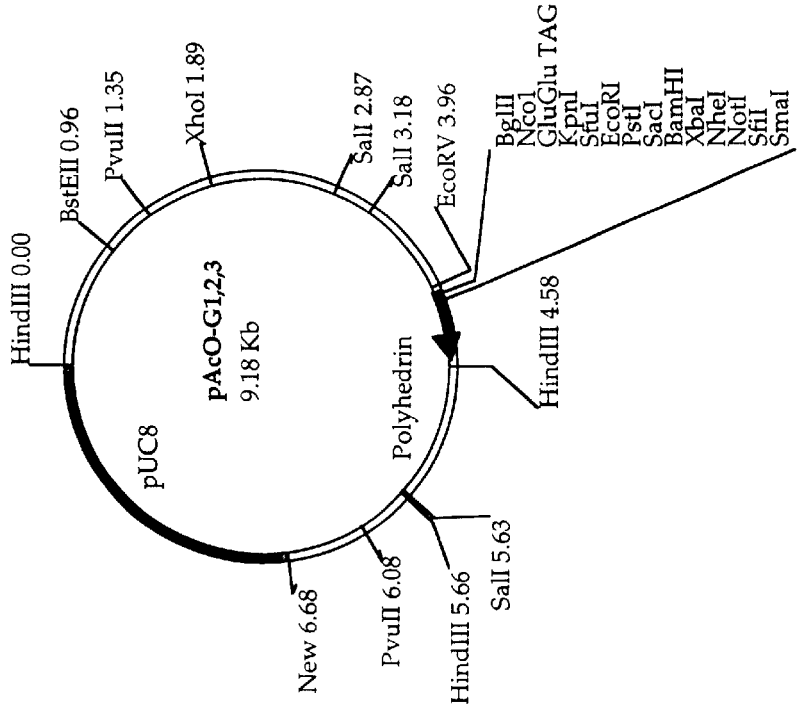

FIGURE 2

SEQUENCE OF MULTIPLE CLONING SITE

```
BglII  NcoI   GLUGLU TAG                                StuI   EcoRI   PstI    SacI   BamHI  XbaI    NheI  NotI  Sfi  SmaI
AAGATCTCCATGGAATACATGGAAGTACTAGGCCTGAATTCCTGCAGAGCTCGGATCCTCTAGAGCTAGCGGCCGCCGGCTACCGACTCTGCT – pAcO-G1

BglII  NcoI   GLUGLU TAG                     KpnI  StuI   EcoRI   PstI    SacI   BamHI  XbaI    NheI  NotI  Sfi  SmaI
AAGATCTCCATGGAATACATGGAAGTACTAGGCCTGAATTCCTGCAGAGCTCGGATCCTCTAGAGCTAGCGGCCGCCGGCTACCGACTCTGCT – pAcO-G2

BglII  NcoI   GLUGLU TAG                  KpnI  StuI   EcoRI   PstI    SacI   BamHI  XbaI    NheI  NotI  Sfi  SmaI
AAGATCTCCATGGAATACATGCAATGAAGAGGTACCAGGCCTGAATTCCTGCAGAGCTCGGATCCTCTAGAGCTAGCGGCCGCCGGGCCCGGGCCGTACCGACTCTGCT – pAcO-G3
```

NUCLEIC ACID THAT ENCODE A CELL GROWTH REGULATORY PROTEIN

This application claims priority from U.S. Provisional Application No. 60/031,266, filed Nov. 15, 1996.

FIELD OF THE INVENTION

The invention described herein relates generally to the field of human disease, and more specifically to treating and diagnosing disease based on nucleic acid sequences that encode a human Cell Growth Regulatory Protein(s) that regulates cell growth by Phosphorylation of cell cycle proteins.

BACKGROUND

Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes. While different types of genetic alterations may all lead to altered expression or function of cell-growth regulatory genes and to abnormal growth, it is generally believed that more than one event is required to lead to neoplastic transformation of a normal cell to a malignant one (Land et al. (1983) *Nature* 304: 596; Weinberg R A (1989) *Cancer Res.* 49: 3713). The precise molecular pathways and secondary changes leading to malignant transformation for most cell types are not clear. A number of cases have been reported in which altered expression or activity of some proteins with putative cell-cycle control functions and/or implicated in the formation of functional transcriptional complexes, such as p53 and RB, can lead to loss of proliferation control in cells (Ullrich et al. (1992) *J. Biol. Chem.* 267: 15259; Hollstein et al. (1991) *Science* 253: 49; Sager R (1992) *Curr. Opin. Cell. Biol.* 4: 155; Levine et al. (1991) *Nature* 351: 453).

Regarding cell cycle aspects of oncogenic transformation, several proteins involved in regulating the cell cycle have recently been identified and shown to be critical regulators of mitosis. The progression of a eukaryotic cell through the cell cycle to mitosis involves a number of what appear to be tightly regulated mutually antagonistic phospatases and kinases. A key kinase this process is cdc2, which is thought to be responsible for initiating mitosis.

Cdc2 is involved in a number of downstream mitotic events including metaphase alignment of chromosomes, segregation of sister chromatids in anaphase, and cleavage furrow formation. A large number of proteins involved in these processes are phosphorylated by cdc2 including histones, lamins and microtubule-associated proteins. See, Nigg, Semin. Cell Biol. 2: 261–270 (1991). Particularly noteworthy is the phosphorylation of caldesmon, an actin-associated protein, which is thought to be necessary for the dissolution of M-phase specific actin cables. Well known changes in nuclear structure also involve cdc2. For instance chromatin condensation involves cdc2 phosphorylation of the histone H1. See, Langan et al. Molec. Cell. Biol. vol. 9: 3860–3868. The dissolution of the nuclear envelope is associated with cdc2 phosphorylation of lamin B. See, Peter, et al. Cell, vol. 61: 591–602 (1990). Further, during mitosis the nucleolus disappears and this event is also associated with cdc2 activity.

Considering the importance of cdc2 to critical cell cycle functions, and therefore to cell growth, one would expect that this enzyme is subject to several significant control mechanisms. Indeed two such mechanisms have been identified and include the phosphorylation of cdc2 at three sites; tyrosine 15, threonine 14 and threonine 161. Phosphorylation of threonine 161 and dephosphorylation of tyrosine 15 and threonine 14 are necessary for kinase activity. The phosphorylation of tyrosine 15 and threonine 14 is thus a negatively regulator of cdc2 kinase activity. See, Mueller, P. R., et al. Science, vol. 270, pages 86–90 (1995). An enzyme termed cyclin-dependent kinase (CDK)-activating kinase (CAK) phosphorylates cdc2 on threonine 161. An enzyme termed Wee1 kinase has been shown to phosphorylate cdc2 at tyrosine 15 but not threonine 14. See, Mueller, P. R., et al. Mol. Biol. Cell vol. 6 page 119 (1995). Recently, a second enzyme has been identified from Xenopus that phosphorylates both amino acids, and has been termed Myt1 for its membrane association, and its capacity to phosphorylate both tyrosine 15 and threonine 14 on cdc2. There is significant nucleotide homology between the Wee1 and Xenopus Myt1 enzymes.

It is worth noting certain other proteins involved in cdc2 action. In order for cdc2 to exhibit kinase activity, and thus phosphorylate its mitotic substrates the phosphates at positions tyrosine 15 and threonine 14 must be removed. This is realized by the phosphatase cdc25. Cdc25 is, in turn, activated by cdc2 phosphorylation. See, Hoffmann, et al., EMBO J. vol: 12; page 53 (1993). Cdc2 is part of a complex consisting of a cyclin, cyclin B. The phosphorylation events that occur on cdc2 occur after its association with cyclin B.

The identification and isolation of a human enzyme with kinase activity similar to Xenopus Myt1 will have significant medical applications both as an inhibitor of uncontrolled cell growth as displayed by cancer cells, and as a means to identify small molecules with similar activity in drug screening assays. Moreover, the enzyme will have diagnostic applications.

SUMMARY OF THE INVENTION

A first object of the invention is to describe a family of related isolated nucleic acid sequences that encode proteins with kinase activity, hereinafter referred to as Cell Growth Regulatory Proteins.

A second object of the invention is to describe a family of related isolated nucleic acid sequences that encode such Cell Growth Regulatory Proteins having molecular weights ranging from about 45–60 kdaltons.

A third object of the invention is to describe an isolated human Cell Growth Regulatory Protein having a calculated molecular weight of about 54.6 kdaltons that phosphorylates Cdc2 of the Cdc2/CyclinB complex at amino acid residues threonine 14 and tyrosine 15, which phosphorylation substantially inhibits the kinase activity of the Cdc2/CyclinB complex.

A fourth object of the invention is to describe isolated nucleic acid sequences that encode protein fragments, or the fragments themselves of Cell Growth Regulatory Protein(s), respectively.

A fifth object of the invention is to describe host cells transformed with isolated nucleic acid sequences that encodes Cell Growth Regulatory Protein(s) or fragments thereof.

A sixth object of the invention is to describe vectors that contain isolated nucleic sequences that encode Cell Growth Regulatory Protein(s) or fragments thereof.

A seventh object of the invention is to describe complexes consisting of full length or fragments of Cell Growth Regulatory Proteins and cell cycle target proteins.

An eighth object of the invention is to describe methods of diagnosing disease, preferably those involving unwanted cell growth, including cancer, using isolated nucleic acid sequences, or fragments thereof, that encode a Cell Growth Regulatory Protein, or fragments thereof.

A ninth object of the invention is a description of antibody that binds to Growth Regulatory Protein, or fragments thereof.

A tenth object of the invention is to describe an assay using isolated nucleic acid sequences that encode a Cell Growth Regulatory Protein, or fragments thereof for identifying compounds that would have therapeutic applications for the treatment of diseases involving unwanted cell growth, including cancer.

These and other objects of the present invention will become apparent to one of ordinary skill in the art upon reading the description of the various aspects of the invention in the following specification. The foregoing and other aspects of the present invention are explained in greater detail in the drawings, detailed description, and examples set forth below.

BRIEF DESCRIPTION OF THE DRAWINGS

FIG. 2 shows the plasmid pAcO-G1, 2, 3 and the multiple cloning site sequence.

DETAILED DESCRIPTION OF THE INVENTION

Figure 1:
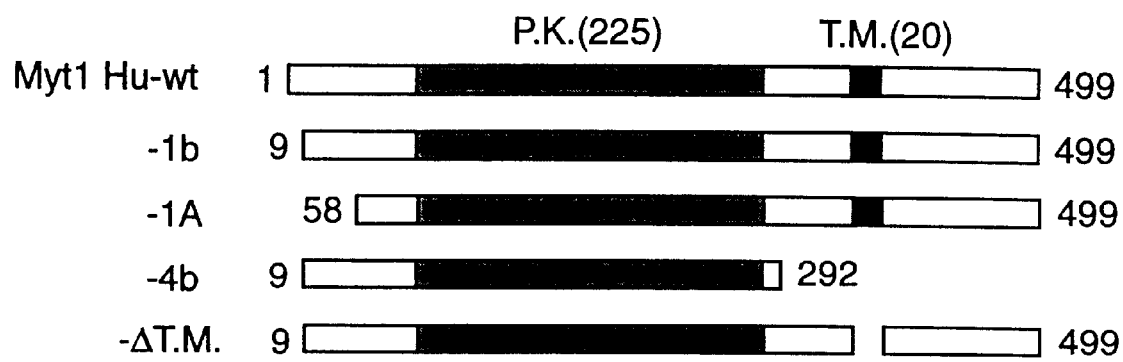
FIG. 1 shows a diagram of the amino acid sequence (Seq I. D. No. 2) of the Cell Growth Regulatory Protein described in Example1 and four truncated Cell Growth Regulatory Protein mutants including deletions of the N-terminus, C-terminus, and the transmembrane segments. The expressed Cell Growth Regulatory Protein proteins contain an N-terminal HA epitope tag and include Cell Growth Regulatory Protein-1b (residues 9–499), Cell Growth Regulatory Protein-1A (residues 58–499), Cell Growth Regulatory Protein-4b (residues 9–292), and Cell Growth Regulatory Protein-ΔT.M. (deleted transmembrane) (residues 9–499 with residues 379–398 deleted).

All publications and patent applications mentioned in this specification are herein incorporated by reference to the same extent as if each individual publication or patent application was specifically and individually indicated to be incorporated by reference.

Definitions

At the outset it is worth noting that unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see generally, Sambrook et al., *Molecular Cloning: A Laboratory Manual, 2nd. edition* (1989) Cold Spring Harbor Laboratory Press, Cold Spring Harbor, N.Y., which is incorporated herein by reference) which are provided throughout this document.

The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

The definitions of the cell cycle, and proteins involved therewith are well known to the skilled practitioner of this art. Briefly, cdc2 and cdc25 are defined as shown by Mueller, P. R., et al. Science, vol. 270, pages 86–90 (1995). Cdc2 associates with cyclin B to form a complex that phosphorylates a number of proteins provided that cdc2 is itself phosphorylated at threonine 161, and dephosphorylated at threonine 14 and tyrosine 15.

In the formulas representing selected specific embodiments of or Cell Growth Regulatory Proteins of the present invention, the amino- and carboxy-terminal groups, although often not specifically shown, will be understood to be in the form they would assume at physiological pH values, unless otherwise specified. Thus, the N-terminal $H_2^+$ and C-terminal-$O^-$ at physiological pH are understood to be present though not necessarily specified and shown, either in specific examples or in generic formulas. In the polypeptide notation used herein, the left-hand end of the molecule is the amino terminal end and the right-hand end is the carboxy-terminal end, in accordance with standard usage and convention. Of course, the basic and acid addition salts including those which are formed at nonphysiological Ph values are also included in the compounds of the invention. The amino acid residues described herein are preferably in the "L" isomeric form. Stereoisomers (e.g., D-amino acids) of the twenty conventional amino acids, unnatural amino acids such as a,a-distributed amino acids, N-alkyl amino acids, lactic acid, and other unconventional amino acids may also be suitable components for polypeptides of the present invention, as long as the desired functional property is retained by the polypeptide. For the peptides shown, each encoded residue where appropriate is represented by a three letter designation, corresponding to the trivial name of the conventional amino acid, in keeping with standard polypeptide nomenclature (described in *J. Biol. Chem.*, 243:3552–59 (1969) and adopted at 37 CFR §1.822(b)(2)).

Free functional groups, including those at the carboxy- or amino-terminus, referred to as noninterfering substituents, can also be modified by amidation, acylation or other substitution, which can, for example, change the solubility of the compounds without affecting their activity.

As employed throughout the disclosure, the following terms, unless otherwise indicated, shall be understood to have the following meanings:

The term "isolated protein" referred to herein means a protein of cDNA, recombinant RNA, or synthetic origin or some combination thereof, which by virtue of its origin the "isolated protein" (1) is not substantially associated with proteins found in nature, (2) is substantially free of other proteins from the same source, e.g. free of human proteins, (3) may be expressed by a cell from a different species, or (4) does not occur in nature.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence from Cell Growth Regulatory Protein that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The phrases "Cell Growth Regulatory Protein," "Cell Growth Regulatory Peptide," or Cell Growth Regulatory Polypeptide" refer to proteins or peptides with kinase activity that regulate cell growth by phosphorylation of proteins that control the cell cycle. Each of these definitions is meant to encompass one or more such entities.

The phrases "cell cycle target," or "cell cycle target gene product" refer to a protein which is phosphorylated by a Cell Growth Regulatory Protein and which is involved in controlling cell growth by affecting the cell cycle. Such "cell cycle targets" may be dimeric; an example is cdc2. Cdc2 requires association with cyclin B to be phosphorylated at threonine 14 and tyrosine 15 by the Cell Growth Regulatory Protein described herein. Each of these definitions is also meant to encompass one or more such entities.

Chemistry terms herein are used according to conventional usage in the art, as exemplified by The McGraw-Hill Dictionary of Chemical Terms (ed. Parker, S., 1985), McGraw-Hill, San Francisco, incorporated herein by reference.

The production of proteins from cloned genes by genetic engineering is well known. See, e.g. U.S. Pat. No. 4,761,371 to Bell et al. at column 6, line 3 to column 9, line 65. (The disclosure of all patent references cited herein is to be incorporated herein by reference.) The discussion which follows is accordingly intended as an overview of this field, and is not intended to reflect the full state of the art.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame.

Suitable host cells include prokaryotes, yeast cells, or higher eukaryotic cells. Prokaryotes include gram negative or gram positive organisms, for example Escherichia coli (E. coli) or Bacilli. Higher eukaryotic cells include established cell lines of mammalian origin as described below. Exemplary host cells are DH5a, E. coli W3110 (ATCC 27,325), E coli B, E. coli X1776 (ATCC 31,537) and E. coli 294 (ATCC 31,446). Pseudomonas species, Bacillus species, and Serratia marcesans are also suitable.

In an insect system, Autographa californica nuclear polyhidrosis virus (AcNPV) may be used as a vector to express foreign genes. (E.g., see Smith et al., 1983, J. Virol. 46: 584; Smith, U.S. Pat. No. 4,215,051). In a specific embodiment described below, Sf9 insect cells are infected with a baculovirus vectors expressing a Cell Growth Regulatory construct with either a 6× histidine tag, myc, or an EE-tag (i.e., Glu-Glu-tag). "E" refers to the amino acid glutamine.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. E. coli is typically transformed using pBR322. See Bolivar et al., Gene 2, 95 (1977). pBR322 contains genes for ampicillin and tetracycline resistance and thus provides easy means for identifying transformed cells. Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., Nature 275, 615 (1978); and Goeddel et al., Nucleic Acids Res. 8, 4057 (1980) and EPO Application Publication Number 36,776) and the tac promoter (H. De Boer et al., Proc. Natl. Acad. Sci. USA 80, 21 (1983)). While these are commonly used, other microbial promoters are suitable. Details concerning nucleotide sequences of many promoters have been published, enabling a skilled worker to operably ligate them to DNA encoding Cell Growth Regulatory Protein in plasmid or viral vectors (Siebenlist et al., Cell 20, 269, 1980)). The promoter and Shine-Dalgarno (SD) sequence (for prokaryotic host expression) are operably linked to the DNA encoding myt 1, i.e. they are positioned so as to promote transcription of the myt 1 messenger RNA from the DNA. The SD sequence is thought to promote binding of mRNA to the ribosome by the pairing of bases between the SD sequence and the 3' end of E. coli 16S rRNA (Steitz et al. (1979). In Biological Regulation and Development: Gene Expression (ed. R. F. Goldberger)). To express eukaryotic genes and prokaryotic genes with a weak ribosome-binding site see Sambrook et al. (1989) "Expression of cloned genes in Escherichia coli." In Molecular Cloning: A Laboratory Manual. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) J. Mol. Biol. 189:113; Tabor et al. (1985) Proc. Natl. Acad. Sci. 82:1074). In addition, a hybrid promoter can also be composed of a bacteriophage promoter and an E. coli operator region (EPO Pub. No. 267,851).

Cell Growth Regulatory Proteins can be expressed intracellularly. A promoter sequence can be directly linked with a Cell Growth Regulatory gene or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase (EPO Pub. No. 219,237).

Cell Growth Regulatory Proteins of the instant invention are membrane associated and display a membrane segment. Such proteins can be generated with or without the membrane segment. To facilitate their purification in those instances where the transmembrane segment is not desired the segment can be removed to yield a soluble cytosolic Cell Growth Regulatory Protein using techniques well known in the art.

Eukaryotic microbes such as yeast cultures may be transformed with suitable vectors containing a Cell Growth Regulatory Protein. See, e.g. U.S. Pat. No. 4,745,057. Saccharomyces cerevisiae is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding Cell Growth Regulatory Protein, sequences for polyadenylation and transcription termination, and a selection gene.

Suitable promoting sequences in yeast vectors include the promoters for metallothionein, 3-phosphoglycerate kinase (Hitzeman et al., J. Biol. Chem. 255, 2073 (1980) or other glycolytic enzymes (Hess et al., J. Adv. Enzyme Reg. 7, 149 (1968); and Holland et al., Biochemistry 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promotes for use in yeast expression are further described in R. Hitzman et al., EPO Publication Number 73,657.

Cultures of cells derived from multicellular organisms are a desirable host for recombinant Cell Growth Regulatory Protein synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See Tissue Culture, Academic Press, Kruse and Paterson, editors (1973).

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Identification of Cell Growth Regulatory Proteins

Cell Growth Regulatory Proteins can be identified using several different techniques for detecting protein-protein interactions. Among the traditional methods which may be employed are co-immunoprecipitation, crosslinking and co-purification through gradients or chromatographic columns of cell lysates or proteins obtained from cell lysates, and to identify proteins in the lysate that phosphorylate target proteins known to regulate cell growth through the cell cycle (i.e. cell cycle target proteins such as cdc2). Such assays may employ full length cell cycle targets or a peptide. Once isolated, such an intracellular Cell Growth Regulatory Protein can be identified and can, in turn, be used, in conjunction with standard techniques, to identify other proteins with which it interacts. For example, at least a portion of an amino acid sequence of an intracellular Cell Growth Regulatory Protein which interacts with a cell cycle target protein can be ascertained using techniques well known to those of skill in the art, such as the Edman degradation technique. (See, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra., and PR Protocols: A Guide to Methods and Applications, 1990, Innis, M. et al., eds. Academic Press, Inc., New York).

Additionally, methods may be employed which result in the simultaneous identification of genes which encode the intracellular proteins interacting with. These methods include, for example, probing expression, libraries, in a manner similar to the well known technique of antibody probing of λgt11 libraries, using labeled protein, or fusion protein, e.g., fused to a marker (e.g., and enzyme, fluor, luminescent protein, or dye), or an Ig-Fc domain.

One method which detects protein interactions in vivo, and which does not rely on the kinase activity of Cell Growth Regulatory Protein, is the two-hybrid system, and is described in detail for illustration only and not by way of limitation. This system has been described (U.S. Pat. No. 5,283,173 Chien et al., 1991, Proc. Natl. Acad. Sci. USA, 88:9578–9582) and is commercially available from Clontech (Palo Alto, Calif.). Briefly, utilizing such a system, plasmids are constructed that encode two hybrid proteins: one plasmid consists of nucleotides encoding the DNA-binding domain of a transcription activator protein fused to a Cell Growth Regulatory nucleotide sequence encoding a Cell Growth Regulatory, or peptide or fusion protein, and the other plasmid consists of nucleotides encoding the transcription activator protein's activation domain fused to a cDNA encoding an unknown protein which has been recombined into this plasmid as a part of the cDNA library. The DNA-binding domain fusion plasmid and the cDNA library are transformed into a strain of the yeast *Saccharomyces cerevisiae* that contains a reporter gene (e.g., HBS or lacZ) whose regulatory region contain the transcription activator's binding site. Either hybrid protein alone cannot activate transcription of the reporter gene; the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, cell cycle proteins that regulate cell growth ((i.e. cell cycle target proteins such as cdc2), or a peptide, or fusion protein derived therefrom may be used as the bait gene product. Total genomic or cDNA sequences are fused to the DNA encoding an activation domain. This library and a plasmid encoding a hybrid of a bait cell cycle target gene product fused to the DNA-binding domain are cotransformed into a yeast reporter strain, and the resulting tranformants are screened for those that express the reporter gene. For example, and not by way of limitation, a bait gene sequence, such as the open reading frame of a cell cycle target protein, or a domain of cell cycle target protein (i.e. a peptide that contains among other amino acids, threonine 14 and tyrosine 15 of cdc2) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait cell cycle target gene product are to be detected can be made using methods routinely practiced in the art. According to the particular system described herein, for example, the cDNA fragments can be inserted into a vector such that they are translationally fused to the transcriptional activation domain of GAL4. This library can be co-transfected along with the bait cell cycle target gene-GAL4 fusion plasmid into a yeast strain which contains a lacZ gene driven by a promoter which contains GAL4 activation sequence. A cDNA encoded protein, fused to GAL4 transcriptional activation domain, that interacts with bait cycle target gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait cycle target gene-interacting protein using techniques routinely practiced in the art.

Whenever a protein is isolated using the two-hybrid assay, an independent assay to ascertain whether the protein has kinase activity is performed. Such assays are well known in the art, and an example is described by Mueller, P. R. et al., Mol. Biol. Cell, vol. 6, page 119 (1995).

Cell Growth Regulatory Protein cDNA

The cDNA, and deduced amino acid sequence, of a representative Cell Growth Regulatory Protein is shown in Seq. ID No. 1. The cDNA encodes a protein that has a calculated molecular weight of 54.6 kd.

The Cell Growth Regulatory Protein nucleotide sequences of the invention include: (a)the human cDNA sequence shown in Seq. ID No. 1 or contained in the cDNA clone as deposited with the American Type Culture Collection under accession number 98169; (b) and any non-Xenopus nucleotide sequence that hybridizes to the complement of the DNA sequence shown in Seq. ID No. 1 or contained in the cDNA clone as deposited with the ATCC accession number 98169 under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green publishing Associates, Inc., and John Wiley & sons, Inc., New York, at p. 2.10.3) and encodes a functionally equivalent gene product; and (c) any non-Xenopus nucleotide sequence that hybridizes to the complement of the DNA sequences that encode the amino acid sequence shown in Seq. ID No. 1 or contained in the cDNA clone as deposited with the ATCC 98169 under less stringent conditions, such as moderately stringent conditions, e.g., washing in 0.2×SSC/0.1% SDS at 42° C. (Ausubel et al., 1989, supra), yet which still encodes a functionally equivalent Cell Growth Regulatory Protein gene product. Functional equivalents include naturally occurring Cell Growth Regulatory Protein genes present in other species, excluding Xenopus, and mutant Cell Growth Regulatory Protein genes whether naturally occurring or engineered which retain at least some of the functional activities of a Cell Growth Regulatory Protein (i.e., binding to). The invention also includes degenerate variants of sequences (a) through (c).

The invention also includes nucleic acid molecules, preferably DNA molecules, that hybridize to, and are therefore the complements of, the nucleotide sequences (a)– through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/ 0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as Cell Growth Regulatory gene antisense molecules, useful, for example, in gene regulation (for and/or as antisense primers in amplification reactions of Cell Growth Regulatory gene nucleic acid sequences). Such sequences may be used as part of ribozyme and/or triple helix sequences, also useful for Cell Growth Regulatory gene regulation. Still further, such molecules may be used as components of diagnostic methods whereby, for example, the presence of a particular Cell Growth Regulatory Protein allele associated with uncontrolled cell growth (i.e. cancer) may be detected.

Further, it will be appreciated by one skilled in the art that a Cell Growth Regulatory Protein gene homolog may be isolated from nucleic acid of an organism of interest by performing PCR using two degenerate oligonucleotide primer pools designed on the basis of amino acid sequences within the Cell Growth Regulatory gene product disclosed herein. The template for the reaction may be cDNA obtained by reverse transcription of mRNA prepared from, for example, human or non-human cell lines or cell types, such as breast or ovarian cells, known or suspected to express a Cell Growth Regulatory gene allele.

The PCR product may be subcloned and sequenced to ensure that the amplified sequences represent the sequences of a Cell Growth Regulatory gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular source (i.e., one known, or suspected, to express a Cell Growth Regulatory Protein gene, such as, for example, from breast or ovarian cells). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

A cDNA of a mutant Cell Growth Regulatory Protein gene may also be isolated, for example, by using PCR. In this case, the first cDNA strand may be synthesized by hybridizing an oligo-dT oligonucleotide to mRNA isolated from cells known or suspected to be expressed in an individual putatively carrying the mutant Cell Growth Regulatory allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant Cell Growth Regulatory allele to that of the normal Cell Growth Regulatory allele, the mutation(s) responsible for the loss or alteration of function of the mutant Cell Growth Regulatory gene product can be ascertained.

A genomic library can be constructed using DNA obtained from an individual suspected of or known to carry the mutant Cell Growth Regulatory allele, or a cDNA library can be constructed using RNA from a cell type known, or suspected, to express the mutant Cell Growth Regulatory allele. The normal Cell Growth Regulatory gene or any suitable fragment thereof may then be labeled and used as a probe to identify the corresponding mutant Cell Growth Regulatory allele in such libraries. Clones containing the mutant Cell Growth Regulatory gene sequences may then be purified and subjected to sequence analysis according to methods well known to those of skill in the art.

Additionally, an expression library can be constructed utilizing cDNA synthesized from, for example, RNA isolated from a cell type known, or suspected, to express a mutant Cell Growth Regulatory allele in an individual suspected of or known to carry such a mutant allele. In this manner, gene products made by the putatively mutant cell type may be expressed and screened using standard antibody screening techniques in conjunction with antibodies raised against the normal Cell Growth Regulatory gene product, as described, below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled fusion proteins. In cases where a Cell Growth Regulatory mutation results in an expressed gene product with altered function (e.g., as a result of a missense or a frameshift mutation), a polyclonal set of antibodies to a Cell Growth Regulatory Protein are likely to cross-react with the Cell Growth Regulatory mutant. Library clones detected via their reaction with such labeled antibodies can be purified and subjected to sequence analysis according to methods well known to those of skill in the art.

The invention also encompasses nucleotide sequences that encode peptide fragments of a Cell Growth Regulatory Protein, truncated Cell Growth Regulatory Proteins, and fusion proteins thereof. Nucleotides encoding fusion proteins may include but are not limited to full length Cell Growth Regulatory Protein, truncated Cell Growth Regulatory Proteins or peptide fragments to an unrelated protein or peptide, such as for example, an epitope tag which aids in purification or detection of the resulting fusion protein; or an enzyme, fluorescent protein, luminescent protein which can be used as a marker. The preferred epitope tag is glu-glu as described by Grussenmyer, T., et al., Proc. Natl. Acad. Sci. U. S. A. vol. 82, pp. 7952–7954 (1985).

The invention also encompasses (a) DNA vectors that contain any of the foregoing Cell Growth Regulatory Protein coding sequences and/or their complements (i.e., antisense); (b) DNA expression vectors that contain any of the foregoing Cell Growth Regulatory Protein coding sequences operatively associated with a regulatory element that directs the expression of the coding sequences; and (c) genetically engineered host cells that contain any of the foregoing Cell Growth Regulatory Protein coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the T7 promoter, baculovirus promoter, cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast-mating factors.

Cell Growth Regulatory Proteins

As mentioned above, Seq. ID No. 1 shows the cDNA, and deduced amino acid sequence, of a representative Cell Growth Regulatory Protein. The protein has a calculated molecular weight 54.6.

The invention Cell Growth Regulatory Proteins, peptide fragments, mutated, truncated or deleted forms thereof and fusion proteins of these can be prepared for a variety of uses, including but not limited to the generation of antibodies, as reagents in diagnostic assays, the identification and/or the interaction with other cellular gene products involved in cell growth, as reagents in assays for screening for compounds that can be used in the treatment of unwanted cell growth disorders, including but not limited to cancer, and as pharmaceutical reagents useful in the treatment of such diseases.

The Cell Growth Regulatory Protein amino acid sequences of the invention include the amino acid sequence shown in Seq. ID No. 1, or the amino acid sequence encoded by the cDNA clone, as deposited with the ATCC, accession number 98169. Further, Cell Growth Regulatory Proteins of other species, excluding Xenopus, are encompassed by the invention. In fact, any Cell Growth Regulatory Protein encoded by the cDNAs described herein, are within the scope of the invention.

The invention also encompasses proteins that are functionally equivalent to the Cell Growth Regulatory Protein encoded by the nucleotide sequence described above and shown in FIG. 1, as judged by any of a number of criteria, including but not limited to the ability to bind to and phosphorylate a cell cycle target, and a change in cellular growth properties or change in phenotype when the Cell Growth Regulatory Protein equivalent is present in an appropriate cell type (i.e. an actively growing cell). Such functionally equivalent Cell Growth Regulatory Protein proteins include but are not limited to additions or substitutions of amino acid residues within the amino acid sequence encoded by the Cell Growth Regulatory Protein nucleotide sequences described, above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to Cell Growth Regulatory Protein DNA (using random mutagenesis techniques well known to those skilled in the art) and the resulting mutant Cell Growth Regulatory Proteins tested for activity, site-directed mutations of the Cell Growth Regulatory Protein coding sequence can be engineered (using site-directed mutagenesis techniques well known to those skilled in the art) to generate mutant Cell Growth Regulatory Proteins with increased function, e.g., altered binding affinity for.

For example, mutant Cell Growth Regulatory Proteins can be engineered so that regions of interspecies identity are maintained, whereas the variable residues are altered, e.g. by deletion or insertion of an amino acid residue(s) or by substitution of one or more different amino acid residues. Conservative alterations at the variable positions can be engineered in order to produce a mutant Cell Growth Regulatory Protein that retains function. Non-conservative changes can be engineered at these variable positions to alter function. Alternatively, where alteration of function is desired, deletion or non-conservative alterations of the conserved regions can be engineered. One of skill in the art may easily test such mutant or deleted Cell Growth Regulatory Proteins for these alterations in function using the teachings presented herein.

Other mutations to a Cell Growth Regulatory Protein coding sequence can be made to generate Cell Growth Regulatory Proteins that are better suited for expression, scale up, etc. in the host cells chosen. For example, the triplet code for each amino acid can be modified to conform more closely to the preferential codon usage of the host cell's translational machinery. Also, the coding sequence can be modified to omit the transmembrane region, thus providing a soluble cytosolic Cell Growth Regulatory Protein.

Peptides corresponding to one or more domains (or a portion of a domain) of a Cell Growth Regulatory Protein, truncated or deleted Cell Growth Regulatory Proteins (e.g., Cell Growth Regulatory Proteins in which portions of one or more of the above domains are deleted) as well as fusion proteins in which the full length of a Cell Growth Regulatory Protein, a Cell Growth Regulatory Protein peptide or truncated Cell Growth Regulatory Protein is fused to an unrelated protein are also within the scope of the invention and can be designed on the basis of a Cell Growth Regulatory Protein nucleotide and Cell Growth Regulatory Protein amino acid sequences disclosed in this Section and above. Such fusion proteins include but are not limited to fusions to an epitope tag (such as is exemplified herein); or fusions to an enzyme, fluorescent protein, or luminescent protein which provide a marker function.

While the Cell Growth Regulatory Proteins and peptides can be chemically synthesized (e.g., see Creighton, 1983, Proteins: Structures and Molecular Principles, W. H. Freeman & Co., N.Y.), large polypeptides derived from the Cell Growth Regulatory Protein and the full length Cell Growth Regulatory Protein itself may advantageously be produced by recombinant DNA technology using techniques well known in the art for expressing nucleic acid containing Cell Growth Regulatory Protein gene sequences and/or coding sequences. Such methods can be used to construct expression vectors containing the Cell Growth Regulatory Protein nucleotide sequences described above and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding Cell Growth Regulatory Protein nucleotide sequences may be chemically synthesized using, for example, synthesizers. See, for example, the techniques described in "Oligonucleotide Synthesis", 1984, Gait, M. J. ed., IRL. Press, Oxford, which is incorporated by reference herein in its entirety.

A variety of host-expression vector systems may be utilized to express the Cell Growth Regulatory Protein nucleotide sequences of the invention. Where a Cell Growth Regulatory Protein peptide or polypeptide is a soluble derivative the peptide or polypeptide can be recovered from the culture, i.e., from the host cell in cases where the Cell Growth Regulatory Protein peptide or polypeptide is not secreted, and from the culture media in cases where a Cell Growth Regulatory Protein peptide or polypeptide is secreted by the cells. However, such engineered host cells themselves may be used in situations where it is important not only to retain the structural and functional characteristics of a Cell Growth Regulatory Protein, but to assess biological activity, e.g., in drug screening assays.

The expression systems that may be used for purposes of the invention include but are not limited to microorganisms such as retrovirus, bacteria (e.g, E. coli, B. subtilis) transformed with recombinant bacteriophage DNA, plasmid DNA or cosmid DNA expression vectors containing Cell Growth Regulatory Protein nucleotide sequences; yeast (e.g., Saccharomyces, Pichia) transformed with recombinant yeast expression vectors containing the Cell Growth Regulatory Protein nucleotide sequences; insect cell systems infected with recombinant virus expression vectors (e.g., baculovirus) containing the Cell Growth Regulatory Protein sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Cell Growth Regulatory Protein nucleotide sequences; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the Cell Growth Regulatory gene product being expressed. For example, when a large quantity of such a protein is to be produced, for the generation of pharmaceutical compositions of Cell Growth Regulatory Protein or for raising antibodies to the Cell Growth Regulatory Protein, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the Cell Growth Regulatory coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). If the inserted sequence encodes a relatively small polypeptide (less than 25 kD), such fusion proteins are generally soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Alternatively, if the resulting fusion protein is insoluble and forms inclusion bodies in the host cell, the inclusion bodies may be purified and the recombinant protein solubilized using techniques well known to one of skill in the art.

In an insect system, *Autographa californica* nuclear polyhedrosis virus (AcNPV) may be used as a vector to express foreign genes. (e.g., see Smith et al., 1983, J. Virol. 46: 584; Smith, U.S. Pat. No. 4,215,051). In a specific embodiment described below, Sf9 insect cells are infected with a baculovirus vectors expressing either a 6×HIS-tagged construct, or an (EE)-tagged Cell Growth Regulatory Protein construct.

In mammalian host cells, a number of viral-based expression systems may be utilized. Specific embodiments described more fully below express tagged Cell Growth Regulatory Protein cDNA sequences using a CMV promoter to transiently express recombinant protein in U937 cells or in Cos-7 cells. Alternatively, retroviral vector systems well known in the art may be used to insert the recombinant expression construct into host cells. For example, retroviral vector systems for transducing hematopoietic cells are described in published PCT applications WO 96/09400 and WO 94/29438.

In cases where an adenovirus is used as an expression vector, the Cell Growth Regulatory Protein nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the Cell Growth Regulatory gene product in infected hosts. (E.g., See Logan & Shenk, 1984, Proc. Natl. Acad. Sci. USA 81:3655–3659). Specific initiation signals may also be required for efficient translation of inserted Cell Growth Regulatory Protein nucleotide sequences. These signals include the ATG initiation codon and adjacent sequences. In cases where an entire Cell Growth Regulatory Protein gene or cDNA, including its own initiation codon and adjacent sequences, is inserted into the appropriate expression vector, no additional translational control signals may be needed. However, in cases where only a portion of the Cell Growth Regulatory Protein coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript may be used. Such mammalian host cells include but are not limited to CHO, VERO, BHK, HeLa, COS, MDCK, 293, 3T3, WI38, and U937 cells.

For long-term, high-yield production of recombinant proteins, stable expression is preferred. For example, cell lines which stably express the Cell Growth Regulatory Protein sequences described above may be engineered.

Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Cell Growth Regulatory Protein gene. Such engineered cell lines may be particularly useful in screening and evaluation of compounds that affect the endogenous activity of the Cell Growth Regulatory Protein gene product.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

The Cell Growth Regulatory Protein gene products can also be expressed in transgenic animals. Animals of any species, including, but not limited to mice, rats, rabbits, guinea pigs, pigs, micro-pigs, goats, and non-human primates, e.g., baboons, monkeys, and chimpanzees may be used to generate Cell Growth Regulatory Protein transgenic animals.

Any technique known in the art may be used to introduce a Cell Growth Regulatory Protein transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the Cell Growth Regulatory Protein transgene be integrated into the chromosomal site of the endogenous Cell Growth Regulatory Protein gene, gene targeting is preferred. Briefly, when such a technique is to be utilized, vectors containing some nucleotide sequences homologous to the endogenous Cell Growth Regulatory Protein gene are designed for the purpose of integrating, via homologous recombination with chromosomal sequences, into and disrupting the function of the nucleotide sequence of the endogenous Cell Growth Regulatory Protein gene. In this way, the expression of the endogenous. Cell Growth Regulatory Protein gene may also be eliminated by inserting non-functional sequences into the endogenous gene. The transgene may also be selectively introduced into a particular cell type, thus inactivating the endogenous Cell Growth Regulatory Protein gene in only that cell type, by following, for example, the teaching of Gu et al. (Gu et al., 1994, Science 265: 103–106). The regulatory sequences required for such a cell-type specific inactivation will depend upon the particular cell type of interest, and will be apparent to those of skill in the art. Once transgenic animals have been generated, the expression of the recombinant Cell Growth Regulatory gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of cell type samples obtained from the animal, in situ hybridization analysis, and RT-PCR. Samples of Cell Growth Regulatory Protein gene-expressing tissue, may also be evaluated immunocytochemically using antibodies specific for the Cell Growth Regulatory Protein transgene product, as described below.

Antibodies to Cell Growth Regulatory Proteins

Antibodies that specifically recognize one or more epitopes of a Cell Growth Regulatory Protein, or epitopes of conserved variants, or peptide fragments are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of the Cell Growth Regulatory Protein in a biological sample and may, therefore, be utilized as part of a diagnostic or prognostic technique whereby patients may be tested for abnormal amounts of these proteins. Such antibodies may also be utilized in conjunction with, for example, compound screening schemes, as described herein for the evaluation of the effect of test compounds on expression and/or activity of the Cell Growth Regulatory Protein. Additionally, such antibodies can be used in conjunction with the gene therapy techniques described herein, to, for example, evaluate the normal and/or engineered Cell Growth Regulatory Protein expressing cells prior to their introduction into the patient. Such antibodies may additionally be used as a method for the inhibition of abnormal Cell Growth Regulatory Protein activity.

For the production of antibodies, various host animals may be immunized by injection with a Cell Growth Regulatory Protein, a Cell Growth Regulatory Protein peptide, truncated Cell Growth Regulatory Protein polypeptides, functional equivalents of the Cell Growth Regulatory Protein or mutants of the Cell Growth Regulatory Protein. Such host animals may include but are not limited to rabbits, mice, and rats, to name but a few. Various adjutants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA, 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against Cell Growth Regulatory Protein gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to the Cell Growth Regulatory Protein can, in turn, be utilized to generate anti-idiotype antibodies that "mimic" the Cell Growth Regulatory Protein using techniques well known to those skilled in the art. (See, e.g., Greenspan & Bona, 1993, FASEB J 7(5):437–444; and Nissinoff, 1991, J. Immunol. 147(8):2429–2438).

Assays for Compounds that Affect Cell Growth Regulatory Protein Activity

As is shown in more detail in the examples, one property of a Cell Growth Regulatory Protein is the capacity to phosphorylate certain proteins that regulate the cell cycle. Indeed, the Cell Growth Regulatory Protein exemplified in Seq. ID No. 1 phosphorylates cdc2 at tyrosine 15 and threonine 14, which phosphorylation blocks cells from entering mitosis. Thus, compounds that affect the phosphorylation of a cell cycle target protein by a Cell Growth Regulatory Protein(s) will affect the cell cycle, and hence cell growth. The extent of the effect will, in large part, depend on the chemical properties of the compounds tested. Some may strongly disrupt the interaction of the cell cycle target protein with a Cell Growth Regulatory Protein, while others would have a minimal effect. The former would be reflected in altered cell growth, while the latter would not. The converse is also true, certain compounds may strengthen the interaction of with Cell Growth Regulatory Proteins, in which case the opposite biological effect would be anticipated. Thus, it is highly desirable to assay for compounds that affect interactions of cell cycle target proteins with Cell Growth Regulatory Proteins.

The basic principle of the assay systems used to identify such compounds that affects interactions of Cell Growth Regulatory Proteins involves preparing a reaction mixture containing cell cycle target protein (i.e. cdc2 complexed to an appropriate cyclin, preferrably cyclin B), polypeptide, peptide or fusion protein of the same, as described above, and a Cell Growth Regulatory Protein under conditions and for a time sufficient to allow the two to interact and for the cell cycle target protein to become phosphorylated. In order to test a compound for activity, either inhibitory or stimulatory, the reaction mixture is prepared in the presence and absence of the test compound. Alternatively, the test compound may be initially included in the reaction mixture, or may be added at a time subsequent to the addition of the cell cycle target protein and a Cell Growth Regulatory Protein. Control reaction mixtures are incubated without the test compound or with a placebo. The amount or rate of phosphorylation of the cell cycle target protein caused by the Cell Growth Regulatory Protein is then detected. An increase in phosphorylation over the control reaction mixture indicates that the compound interacts with the reactants to enhance phosphorylation of the cell cycle target protein. Controls can be run to ensure that the test compounds are not causing dephosphorylation of the cell cycle target protein. Such compounds would be useful since they would mimic or enhance the effect of Cell Growth Regulatory Proteins, and thus have applications as anticancer therapeutics. Additionally, phosphorylation in reaction mixtures containing the test compound and normal, or wild type, Cell Growth Regulatory Protein may also be compared to phosphorylation in reaction mixtures containing the test compound and a mutant Cell Growth Regulatory Protein. This comparison may be important in those cases where it is desirable to identify compounds that affect phosphorylation of cell cycle target proteins by mutant but not normal Cell Growth Regulatory Protein.

The assay for compounds that interfere with, or stimulate the phosphorylation of a cell cycle target protein by a Cell Growth Regulatory Protein can be conducted in a heterogeneous or homogeneous format. Heterogeneous assays will generally involve anchoring the cell cycle target protein onto a solid phase and detecting phosphorylated complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the cell cycle target protein and interactive Cell Growth Regulatory Protein. Alternatively, test compounds that disrupt preformed complexes, e.g., compounds with higher binding constants that displace one of the components from the complex, can be tested by adding the test compound to the reaction mixture after complexes have been formed. Representative formats are described briefly below.

In a heterogeneous assay system, the cell cycle target protein is anchored onto a solid surface, while the non-anchored Cell Cycle Regulatory Protein is used to phosphorylate the target protein. In practice, microtiter plates are conveniently utilized. The anchored species may be immobilized by non-covalent or covalent attachments. Non-covalent attachment may be accomplished simply by coating the solid surface with a solution of the cell cycle target protein and drying. Alternatively, an immobilized antibody specific for the species to be anchored, that is, the cell cycle target protein, may be used to anchor it to the solid surface. The surfaces may be prepared in advance and stored.

In order to conduct the assay, the partner of the immobilized species, that is, the Cell Cycle Regulatory Protein, is exposed under proper reaction conditions to the coated surface with or without the test compound. After the reaction is complete, unreacted components are removed (e.g., by washing) and any phosphorylated complexes formed will remain immobilized on the solid surface. The detection of complexes anchored on the solid surface can be accomplished in a number of ways. Generally, radiolabelled phosphate transferred from gamma-labeled $^{32}$P-ATP is measured. Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

Alternate embodiments of the homogeneous assay are shown in U.S. Pat. No. 4,109,496 by Rubenstein.

In a particular embodiment, a fusion protein can be prepared for immobilization. For example, a cell cycle target protein, or a peptide fragment therefrom, can be fused to a glutathione-S-transferase (GST) gene using a fusion vector, such as pGEX-5X-1, in such a manner that its ability to be phosphorylated is maintained in the resulting fusion protein. In a heterogeneous assay, e.g., the GST-fusion protein can be anchored to glutathione-agarose beads. The Cell Growth Regulatory Protein can then be added in the presence or absence of the test compound in a manner that allows binding and phosphorylation to occur. At the end of the reaction period, unbound material can be washed away, and the labeled cell cycle target protein detected. The interaction between the cell cycle target protein and the Cell Growth Regulatory Protein can be detected by measuring the amount of radioactivity that remains associated with the glutathione-agarose beads. A successful inhibition of the interaction by the test compound will result in a decrease in measured radioactivity.

Alternatively, the GST-fusion cell cycle target protein and the Cell Growth Regulatory Protein can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the cell cycle target protein/Cell Growth Regulatory Protein interaction can be detected by measuring the radioactivity associated with the beads.

In another embodiment of the invention, these same techniques can be employed using peptide fragments that correspond to the phosphorylation domains of the cell cycle target protein. Any number of methods routinely practiced in the art can be used to identify and isolate the domains. Such domains are discussed more fully in the examples, below, and for cdc2, consist of the ATP binding domain. These methods include, but are not limited to mutagenesis of the gene encoding one of the proteins and screening for disruption of binding in a co-immunoprecipitation assay.

Using the above described approach, Cell Growth Regulatory Protein domains involved in phosphorylation cell cycle target proteins can be identified. Compensating mutations in the gene can then be selected. Sequence analysis of the genes encoding the respective proteins will reveal the mutations that correspond to the region of the protein involved in the phosphorylation reaction. The two hybrid assay may also be used, as discussed more fully in the examples below. For instance, once the gene coding for a Cell Growth Regulatory Protein is obtained, short gene segments can be engineered to express peptide fragments of the protein, which can then be tested for phosphorylation activity and purified or synthesized.

Effective Dose

Toxicity and therapeutic efficacy of compounds identified above that affect the interaction of cell cycle target proteins with Cell Growth Regulatory Proteins, and thus affect cell growth can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Numerous model systems are known to the skilled practitioner of the art that can be employed to test the cell growth properties of the instant compounds including growth of cells in soft agar, and effect on tumors in vivo. Such experiments can be conducted on cells co-transfected with and Cell Growth Regulatory Proteins.

The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The Examples which follow are illustrative of specific embodiments of the invention, and various uses thereof. They are set forth for explanatory purposes only, and are not to be taken as limiting the invention

EXAMPLE 1

Cloning of cDNA that Encodes Cell Growth Regulatory Protein

A Cell Growth Regulatory Protein was identified in a human placental cDNA library as follows. A TBLASTN search of the dbEST was performed using the amino acid sequence encoded by Xenopus Cell Growth Regulatory Protein. See, Mueller al (1995) Science 270, pp 86–90. As expected, the majority of high-scoring matches were protein kinases, owing to the extensive conservation of residues within the catalytic domain of protein kinases (Hanks et al., (1988) *Science* 42–52). However, two nearly identical human ESTs (dbEST Id: 336264 and 335241) were found to match significantly amino acid tracts within the C-terminal (non-catalytic domain) 130 residues of the Xenopus-Cell Growth Regulatory Protein kinase. A 325-bp DNA fragment corresponding to an internal region of EST clones 335241 and 336264 was PCR-generated, using oligos 5'-AGCAGCCTCTCCAGCAACTGG-3' (Seq. ID No.3) and 5'-CAGAGAAGACCATGGAGTTCC-3' (Seq. ID No.4) (5' and 3' primers, respectively) and the first strand cDNA synthesis of fetal brain RNA (Clonetech) as template. This DNA fragment was $^{32}$P-labeled by random priming (Pharmacia) and used as a probe to screen approximately $7 \times 10^5$ clones of a human placental Lamda ZAPII cDNA library (Stratagene Corporation). Of the 9 positives isolated, clone 16 was found to contain the longest cDNA insert, a 1.98-kb cDNA, and the complete DNA sequence of this clone was determined using an ABI sequence. The 1.98-kb cDNA is approximately the size of the Cell Growth Regulatory Protein transcript observed by Northern blotting. Sequence analysis of this clone revealed a 1497-bp open reading frame that is predicted to encode a 499-aa kinase with a calculated molecular mass of 54.6 kDA. We cannot exclude the possibility that this cDNA encodes a 490 aa protein since a second AUG codon, in an equally favorable initiator context, is present 9 codons downstream from the first AUG. Regardless, an aspect of the instant invention is the 1497-bp cDNA whether it encodes a 499-aa or 490-aa protein. This cDNA is on deposit with the American Type Culture Collection under accession number 98169.

EXAMPLE 2

Properties of Cell Growth Regulatory Protein

The Cell Growth Regulatory Protein described in Example 1, and encoded by the cDNA on deposit with the American Type Culture Collection under accession number 98169, was tested for kinase activity by its capacity to inactivate Cdk/cyclin complexes in a cell-free extract system. The baculovirus expression system described in Example 3 was used to produce insect cell extracts that contained high levels of human Cdk, cyclin, Wee1, and the Cell Growth Regulatory Protein. The production of these proteins are either known in the art, or described in the following Examples. It is known previously that Cdk/cyclin kinase activation can be reconstituted upon mixing individual Cdk and cyclin-containing lysates (Desai et al. (1992) Mol.Biol. Cell 571–582); thus, if the Cell Growth Regulatory Protein encodes a kinase that inhibits the activity of the Cdk/cyclin complex, this would be readily detected by performing the appropriate phosphorylation assays.

We first assessed the ability of this assay to detect Wee1 activity. Wee1 is a kinase that is known to phosphorylate Cdc2/CyclinB1, but it phosphorylates only one residue on Cdc2, and that is Tyrosine-15. Thus, experiments were conducted to compare and contrast its phosphorylation pattern of Cdc2 to that produced by the Cell Growth Regulatory Protein.

Lysates containing wild-type Cdc2 were mixed with Cyclin B1 lysates and with either mock-infected or Wee1-containing lysates. After a brief incubation, an aliqout of this lysate mixture was removed and Cdc2/CyclinB1 kinase activity was determined by performing a histone H1 kinase reaction, as described by Booher et al. (1993) EMBO J. vol. 12: 3417–3426. It was observed that the addition of Wee1 lysates effectively inhibited Cdc2/CyclinB1 kinase activation. Also, the Wee1 inhibitory activity was dependent on the presence of the phosphorylatable Tyrosine-15 residue in Cdc2, since the mutant constructs, Cdc2-F15/CyclinB1 and Cdc2-AF/CylinB1 complexes retained full activity in the presence of Wee1 lysates.

When Cell Growth Regulatory Protein lysates were combined together with wild-type Cdc2 and CyclinB1-containing lysates, a dramatic reduction in Cdc2 kinase activation was observed, similar to that observed for Wee1. Furthermore, such lysates also inhibited both Cdc2-A14 and Cdc2-F15 activation indicating that the Cell Growth Regulatory Protein can phorphorylate either Threonine 14 or Tyrosine 15 inhibitory sites in Cdc2; though, Cell Growth Regulatory Protein preferentially phosphorylates Threonine 14 since Cdc2-A14 lysates consistently retain some histone H1 kinase activity. Immunoblotting of the Cell Growth Regulatory Protein/Cdc2/CyclinB1 mixed lysates, using phosphotyrosine antibodies as probes (Wong et al. (1992) Cell vol. 69: 551–558, and New England Biolabs Catalogue) showed that Cdc2 was phosphoryalted on Tyrosine 15 to some extent.

Human Wee1 is capable of phosphorylating Cdk2/cyclin A and Cdk2/cyclin E complexes in vitro. To determine whether the Cell Growth Regulatory Protein can also inactivate the Cdk2/cyclin complex, the histone H1 kinase in Cdk2 lysates that had been activated in the presence of Cell Growth Regulatory Protein containing lysates was measured. A Cdk2-AF mutant was used as a reference to control for any non-Threonine 14 or Tyrosine 15 phosphorylation inhibitory activity that may be present in the Cell Growth Regulatory Protein lysate. The results showed an equivalent amount of histone H1 kinase activity was present in wild-type Cdk2 and Cdk2-AF lysates that had been mixed with either cyclin A or cyclin E lysates in the presence of Cell Growth Regulatory Protein, indicating that neither Cdk2/cyclin A nor Cdk2/cyclin E complexes are negatively regulated by the Cell Growth Regulatory Protein.

Additional experiments whether done to determine if the Cell Growth Regulatory Protein would inhibit Cdc2/cyclin A activation. Analysis of a Cell Growth Regulatory Protein/Cdc2/cyclin A mixed lysate revealed that it had greatly reduced histone H1 kinase activity compared to a mock-treated or Cdc2-AF control lysate. Thus, Cell Growth Regulatory Protein can readily inhibit Cdc2/cyclin A activation. A simple interpretation of these results is that the Cdk subunit, not the cyclin subunit, is a key determinant for whether a particular Cdk/cyclin complex is recognized by the Cell Growth Regulatory Protein kinase.

Additional experiments were conducted on the kinase substrate specificity by testing whether Cell Growth Regulatory Protein could phosphorylate directly various Cdk/cyclin complexes. For these experiments, various combinations of affinity purified Cell Growth Regulatory Protein, Wee1, and Cdk/cyclin complexes were incubated together in a kinase reaction containing [gamma-$^{32}$P]ATP followed by SDS-PAGE analysis of the $^{32}$P-labeled proteins. These experiments showed that both purified Cell Growth Regulatory Protein and Wee1 kinases were capable of phosphorylating wild-type Cdc2 as well as a kinase-deficient Cdc2 mutant (K–), each of which was complexed with cyclin B1. It was further determined that the Cdc2-AF mutant was not phosphorylated by Cell Growth Regulatory Protein or Wee1, indicating that these kinases were phosphorylating either Cdc2 residue Threonine 14, or Tyrosine15, or both. A low level of $^{32}$P-labeled Cdc2 was also detected in the untreated wild-type Cdc2/cyclin B1 kinase reaction. The basis of this Cdc2 phosphorylation is unknown but a similar observation has been reported by Watanabe et al. (1995) EMBO J. vol. 14: 1878–1891. It should also be noted that we used a truncated Wee1 kinase in these studies because an unidentified 40 kD protein, which became highly $^{32}$P-labeled in the Cdc2/cyclin B1 kinase reaction, co-purified with full-length Wee1 during affinity chromatography from Sf9 cell lysates.

Further experiments showed that when Cdk2/cyclin complexes were used as substrates in these kinase reactions, Cell Growth Regulatory Protein failed to phosphorylate Cdk2 that was complexed with either cyclin A or cyclin E. In contrast, Wee1 readily phosphorylated Cdk2 that was complexed with either cyclin A and cyclin E, which is consistent with the findings of Watanabe et al. (1995) EMBO J. vol. 14: 1878–1891. We also tested a Cdk4/cyclin D1 complex and found that neither Cell Growth Regulatory Protein nor Wee1 phosphorylated the Cdk4 subunit.

Thus, the above results establish that using either a crude lysate system or an in-vitro kinase reaction using purified components, it was consistently observed that Cell Growth Regulatory Protein only phosphorylated and inactivated Cdk/cyclin complexes in which Cdc2 was the catalytic subunit Because the above experiments with Cell Growth Regulatory Protein were done on Cdc2 complexed to cyclins, experiments were conducted to assess whether Cell Growth Regulatory Protein phosphorylation of Cdc2 requires cyclin association. Thus, a experiment was performed with Cell Growth Regulatory Protein and monomeric Cdc2 as substrate. The results showed that Cell Growth Regulatory Protein did not phosphorylate monomeric Cdc2. However, reconstitution of the Cdc2/cyclin B1 complex, by pre-incubating monomeric Cdc2 with monomeric cyclin B1, enabled Cell Growth Regulatory Protein to phosphorylate Cdc2, indicating that Cell Growth Regulatory Protein can only phosphorylate Cdc2 that is complexed with a cyclin subunit. For comparison, similar experiments were conducted with the truncated Wee1 kinase, and it was observed that it was capable of $^{32}$P-labeling monomeric Cdc2, but this phosphorylation was enhanced when the cyclin-bound form was reconstituted, which is consistent with previous studies. See, Parker et al. (1995) PNAS vol. 92: 9638–9642.

Because Cell Growth Regulatory Protein failed to phosphorylate Cdc2-AF complexed with cyclin B1, it must phosphorylate wild-type Cdc2 on either Threonine 14 or Tyrosine 15, or both. Phosphoamino acid analysis of Cdc2 that had been $^{32}$P-labeled by Cell Growth Regulatory Protein revealed that phosphorylation occurred only on threonine residues, indicating that Cdc2-Threonine14 was the sole site of Cell Growth Regulatory Protein phosphorylation. The absence of phosphotyrosine is unlikely due to the use of the Cdc2(K–) mutant since the Tyrosine 15 residue was readily phosphorylated by full-length Wee1. Further phosphoamino analysis revealed that Cell Growth Regulatory Protein autophosphorylated itself on tyrosine, threonine, and serine residues, while full-length Wee1 only contained phosphotyrosine.

EXAMPLE 3

Expression of Cell Growth Regulatory Proteins

The Cell Growth Regulatory Proteins were generally expressed in and purified from baculovirus Sf9 infected cells. Methods for expressing proteins in baculovirus, as well as growing Sf9 cells are well known in the art, and detailed procedures can be found in M. Summers and G. Smith in "A Manual of Methods for Baculovirus Vectors and Insect Cell Culture Procedures," Texas Agricultural Experiment Station, Bulletin No. 1555 (May, 1987 or in EPS 127,839 to G. E. Smith and M. D. Summers. Depending on the protein expressed, a preferred construct was generated and used to express the protein in Sf9 cells. These are as follows.

Cell Growth Regulatory Protein Baculovirus Expression Vector: A Cell Growth Regulatory Protein-containing DNA fragment corresponding to base-pairs 354–1925 (numbering according to FIG. 1) was PCR amplified using cDNA clone 16 as template and the 5' primer 5'-TCGAATTCATGCCCATGCCCACG-3' (Seq. ID No. 5), corresponding to bases 353–368 bases and the 3' primer 5'-CAGAGAAGACCATGGAGTTCC-3' (Seq. ID No. 4), corresponding to the reverse complement of bases 1904–1925; and introduced EcoRI restriction site within the 5' primer is italicized. This PCR fragment was cloned by T-cloning into vector pT7Blue (Novagen). An EcoRI-XbaI Cell Growth Regulatory Protein-containing DNA fragment was isolated from this vector and inserted into the EcoRI and XbaI sites of the baculovirus transfer vector pAcO-G1. This vector was generated from pAcOG, a derivative of pAcC13 (See, FIG. 2, and Rubinfeld, B., et al. Cell 65, 1033–1042 (1991)) in which the polylinker in pAcC13 was replaced with a synthetic linker engineered to encode an initiating methionine, the Glu-Glu (See, Grussenmyer, T., et al. Proc. Natl. Acad. Sci. U.S.A. 82, 7952 (1985)) epitope tag, and a multiple cloning site containing several stop codons (See, Rubinfeld, B., et al. J. Biol. Chem, 270, 5549–5555 (1995)). The baculovirus expression vector, pAcO-G1, expresses a truncated Cell Growth Regulatory Protein hybrid protein (residues 1–9 deleted) that is fused with an N-terminal 12-residue peptide (MEYMPMEGTRPE) (Seq. ID No. 6).

The Glu-Glu epitope tag facilitates purification of the Cell Growth Regulatory Protein fragment by antibody affinity as described below in Example 4. Wee1 Baculovirus Expression Vector: The full-length human Wee1 coding region, corresponding to base-pairs 254–2194 (numbering according to Watanabe et al. (1995) EMBO J. VOL. 14: 1878–1891), was isolated from the Wee1-containing clone 1E-12 [Watanabe, et al] and inserted into the baculovirus transfer vector pAcO-G1. This baculovirus expression vector expresses Wee1 protein that is fused with an N-terminal 23-residue peptide (MEYMPMEGTRPEFELGTRGSDWS) (Seq. ID No. 7) that contains the Glu-Glu epitope tag. Additionally, Wee1 residue Serine 2 was changed to glycine. A baculovirus expression vector expressing a truncated Wee1 protein was constructed by inserting a Wee1-containing DNA fragment corresponding to base-pairs 896–2194 (numbering according to Wanatabe et al.) into pAcO-G3 (FIG. 2). This recombinant Wee1 protein is fused with an N-terminal 17-residue peptide (MEYMPMEEVPGLNSAWS) (Seq. ID No. 8) that contains the Glu-Glu epitope tag.

Cdk Baculovirus Expression Vector: Baculovirus expression vectors expressing C-terminal influenza hemagglutinin (HA)-tagged Cdc2-wt, F15, AF, and K– proteins, and C-terminal HA-tagged Cdk2-wt and AF proteins were all provided by Dr. David Morgan (UCSF) and have been previously described [Desai et al (1992) Mol Biol Cell 3:571–582; Gu et al. (1992) EMBO J., 11:3995–4005]. It may be noted that F15, AF, and K– refers to mutants of Cdc2. In some cases the HA-tag was replaced with a 12-residue peptide, TMEYMPMEGYQA (Seq. ID No. 9) for Cdc2 and SMEYMPMEGYQA (Seq. ID No. 10) for Cdk2, by inserting the respective coding regions into the baculovirus expression vector pAcO-C2 (FIG. 2). The Cdc2-A14 mutation (Threonine 14 to Alanine) was created by site-directed oligo mutagenesis.

Cyclin Baculovirus Expression Vector: The human cyclinA coding region was inserted into baculovirus expression vector pAcO-G3 such that the expressed cyclinA protein is fused at the N-terminus with a 20-residue peptide. (MEYMPMEEVPGLNSCSPGAV) (Seq. ID No. 11). The human cycin A coding region is described by Pines and Hunter (1990) Nature, vol. 346: 760–763. A PstI-SacI DNA frament containing the entire CyclinA coding region was cloned into PstI/SacI-cut baculovirus transfer vector pAcO-G3. The human cyclinB coding region was also inserted into pAcO-G3 and this expresses cyclinB1 protein that contains an N-terminal 20-residue peptide (MEYMPMEEVPGLNSCRARIS) (Seq. ID No. 12). The cyclinB1 coding region is described by Pines and Hunter (1989) Cell, vol.58: 833–846. The coding region is contained in a 1.5 kb DNA fragment which was cloned into BamHI/NotI cut baculovirus transfer vector pAcO-G3. The human cyclinE coding region was cloned into pAcO-G1 and was expressed with an N-terminal 21-residue peptide (MEYMPMEGTRPEFRDAKERDT) (Seq. ID No. 13). The CyclinE coding region is described by Koff et al. (1991) Cell, vol, 66: 1217–1228. An EcoRI-EcoRV DNA fragment containing the entire Cyclin E coding region was cloned into EcoRI/SmaI cut baculovirus transfer vector pAcO-G1. Each of these N-terminal peptides contain the Glu-Glu epitope. The GST-cyclinB1 baculovirus expression vector expresses cyclinB1 with an N-terminal glutathione S-transferase fusion.

EXAMPLE 4

Purification of Cell Growth Regulatory Protein

Large-scale production of heterologous proteins in Sf9 cells with recombinant baculoviruses and subsequent purification of Glu-Glu-tagged proteins was performed as follows. The Cdk/cyclin complexes were activated by mixing separate Cdk and cyclin-containing Sf9 extracts together with CAK (Cdk7/cyclin H; see, Fisher and Morgan (1994) Cell, vol, 78; 713–724) and ATP prior to purification. Briefly, baculovirus containing the appropriate construct was produced by transfecting the above described plasmids into SF9 cells, and isolating the corresponding baculovirus using essentially the methods described in Pharmingen's cat. no. 21100D, BaculoGoldtm/Baculovirus DNA. Virus was isolated from individual plaques, and used to infect Sf9 cells. The cells were grown for 4 days, isolated by centrifugation, and cell extracts made by solubilizing the cell pellet. Briefly, recombinant Sf9 cells were pelleted, lysed in 5 volumes of [20 mM Tris (pH8.0), 1 mM EDTA, 10 mg/ml each of leupeptin, pepstatin, pefabloc, 1 mM aprotinin and 1 mM DTT] and incubated on ice for 10 minutes. NaCl was then added to a final concentration of 150 mM, incubated at room temperature for 10 minutes and centrifuged. The resulting supernatant was loaded onto a 1-ml affinity column containing a mouse Glu-Glu monoclonal antibody covalently cross-linked to protein G-Sepharose. See, Grussenmyer, T., et al., Proc. Natl. Acad. Sci. U. S. A. vol.82, pp. 7952–7954 (1985). The column was washed with 10–15 ml of lysis buffer and eluted with 100 mg of Glu-Glu peptide (EYMPME) per ml in the same buffer. Fractions were collected and analyzed by sodium dodecyl sulfate-polyacrylamide gel electrophoresis (SDS-PAGE), the peak fractions were pooled and based on purity subjected to further purification on HPLC columns which include Resource Q, Resource S and Resource Eth (Pharmacia). For purification of insoluble proteins, in particular 091-21A31, Sequence ID No. 1, recombinant Sf9 cells were pelleted, lysed in 5 volumes of [20 mM Tris (pH8.0), 137 mM NaCl, 1 mM EGTA, 1.5 mM $MgCl_2$, 2%SDS, 10 mg/ml each of leupeptin, pepstatin, pefabloc, 1 mM aprotinin and 1 mM DTT], incubated at room temperature for 20–30 minutes and ultra centrifuged. The upper phase was removed, NaCl was adjusted to 400 mM and recentrifuged. The clarified supernatant was then diluted 1:10 in 1×TG buffer [20 mM Tris (pH8.0), 137 mM NaCl, 1 mM EGTA, 1.5 mM $MgCl_2$, 1% Triton X100, 10% glycerol, 10 mg/ml each of leupeptin, pepstatin, pefabloc, 1 mM aprotinin and 1 mM DTT], filtered through a 3 uM Gelman Versapore filter and loaded onto a 1-ml anti-Glu-Glu affinity column. See, Rubinfeld, B., et al., Mol. Cell. Bio. 12, 4634–4642 (1992). The column was washed with 10–15 ml of 1×TG buffer with 400 mM NaCl and eluted in 1×TG buffer with 1% SDS and 100 mg/ml Glu-Glu peptide. Fractions were analyzed by SDS-PAGE.

EXAMPLE 5

Preparation of Antibody to Cell Growth Regulatory Protein

Polyclonal rabbit antibodies were raised against three different Cell Growth Regulatory Protein specific peptides. Each of the peptides was conjugated to maleimide activated KLH (Pierce) prior to immunization. Rabbits 12390 and 12391 were injected with peptide C-47 corresponding to amino acids 472–487 (CNSEPPRGSFPSFEPRN) (Seq. ID No. 14) near the C-terminus of Cell Growth Regulatory Protein. Rabbits 12392 and 12393 were injected with peptide C-49 corresponding to amino acids 486–499 (CRNLLSMFEDTLDPT) (Seq ID No. 15) at the C-terminus of Cell Growth Regulatory Protein. Rabbits 12400 and 12401 were injected with peptide C-48 corresponding to amino acids 10–23 (MPMPTEGTPPPLSGC) (Seq. ID No.

16) near the N-terminus of Cell Growth Regulatory Protein. The Cell Growth Regulatory Protein peptides were synthesized by Multiple Peptide Systems and the rabbit polyclonal antibodies were generated at Pocono Rabbit Farm and Laboratory, Inc. These antibodies were used to determine the cellular location of Cell Growth Regulatory Protein, as described in Example 7.

EXAMPLE 6

Cell Growth Regulatory Proteins that Lack a Trans-Membrane Region

The Cell Growth Regulatory Protein encoded by the cDNA sequence shown in Example 1 (American Type Culture Collection, Accession Number 98169) contains a predicted 20 amino acid transmembrane segment just C-terminal of the kinase catalytic domain (Mueller al (1995) Science 270, pp 86–90). To determine if this segment directs this Cell Growth Regulatory Protein to membranes, we expressed a series of Cell Growth Regulatory Protein deletion mutants in mammalian cells and assessed their ability to associate with the membrane fraction by immunoblotting. Four truncated Cell Growth Regulatory Protein mutants were constructed and included deletions of the N-terminus, C-terminus, and the transmembrane segments. These constructs are shown schematically in FIG. 2. The expressed Cell Growth Regulatory Protein forms include Cell Growth Regulatory Protein-1b (residues 9–499), Cell Growth Regulatory Protein-1A (residues 58–499), Cell Growth Regulatory Protein-4b (residues 9–292), and Cell Growth Regulatory Protein-ΔT.M. (residues 9–499 with residues 379–398 deleted). They were generated as follows.

Protein-1b, A Cell Growth Regulatory Protein-containing DNA fragment (bases 353–1925, numbering according to Seq. ID No. 1) was PCR-amplified using cDNA clone 16 as template and the 5' primer 5'-TCGGATCCATGCCCATGCCCACG-3' (Seq. ID No. 17), corresponding to bases 353–368 bases and the 3' primer 5'-CAGAGAAGACCATGGAGTTCC-3' (Seq. ID No.4), corresponding to the reverse complement of bases 1904–1925; an introduced BamHI restriction site within the 5' primer is italicized. This PCR fragment was cloned by T-cloning into vector pT7Blue (Novagen). An EcoRI-XbaI Cell Growth Regulatory Protein-containing DNA fragment was isolated from this vector and inserted into the EcoRI and XbaI sites of the baculovirus transfer vector pCAN-HA1. Protein-1A, an EcoRI DNA fragment containing the Cell Growth Regulatory Protein corresponding to base-pairs 547–1976 (obtained from a partial cDNA clone in vector pZAPII) was cloned into the EcoRI site of vector pCAN-HA1. This clone contains approximately 20 additional base-pairs within the 3' non-coding region. Protein-4b, a Cell Growth Regulatory Protein-containing DNA fragment (bases 353–1355, numbering according to FIG. 1) was PCR-amplified using cDNA clone 16 as template and the 5' primer 5'-TCGGATCCATGCCCATGCCCACG-3' (Seq. ID No.17), corresponding to bases 353–368 bases and the 3' primer 5'-CAGAGAAGACCATGGAGTTCC-3', corresponding to the reverse complement of bases 1340–1355; and introduced BamHI restriction site within the 5' primer is italicized. This PCR fragment was cloned by T-cloning into vector pT7 Blue (Novagen). An EcoRI-XbaI Cell Growth Regulatory Protein-containing DNA fragment was isolated from this vector and inserted into the EcoRI and XBaI sites of the baculovirus transfer vector pCAN-HA1. Protein-Δ.T.M., a BamHI DNA fragment containing the analogous Protein-1b coding region, except that base-pairs 1462–1518 were deleted by oligo mutagenesis, was cloned into the BamHI site of vector pCAN-HA1.

As noted, each truncated form was fused at the N-terminus with the hemagglutinin (HA) epitope tag (See, Field et al. (1988) Mol. Cell. Biol., vol. 8: 2159–2165) thus permitting specific detection of the transiently expressed gene product by probing immunoblots with the Mab 12CA5 which recognizes the hemagglutinin epitope tag (See, Wilson et al. (1984) Cell, vol. 37: 767–778). These plasmids were transiently transfected into human C33A cells using standard techniques, followed by immunoblot analysis of the soluble and membrane fractions. Briefly, transient transfections of C33A cells were done on cells grown in DME, supplemented with fetal calf serum and 10% BSA, using the calcium phosphate precipitation DNA transfection protocol. The S100 and P100 fractions (100,000 g supernatant and pellet) were prepared from cells (48 hr post-transfection) that had been lysed by dounce homogenization in an ice-chilled hypotonic buffer (10 mM Hepes, pH 7.5,5 mM KCl, 1.5 mM $MgCl_2$, protease inhibitors). The membrane-bound proteins in the P100 fractions were solubilized by extracting the P100 pellets with 1% NP40.

The results showed that both of the N-terminal truncation mutants (-1b and -1A) were present solely in the membrane fraction whereas the two C-terminal mutants (–4b, and -ΔT.M.) were present in the cytosol. These transiently expressed proteins comigrated exactly with the analogous proteins expressed in a coupled transcription/translation system. These results demonstrate that the human Cell Growth Regulatory Protein localizes to membranes via the C-terminal 20-aa transmembrane segment.

Moreover, additional experiments established that the Cell Growth Regulatory Proteins-1b and ΔT. M. exhibit kinase activity. Thus, these constructs will have utility in the assays described below that are aimed at identifying compounds with prophylactic or therapeutic activity for treating diseases arising from unwanted cell growth.

EXAMPLE 7

Phosphorylated Cell Growth Regulatory Protein

Experiments were conducted to show that the Cell Growth Regulatory Protein encoded by the cDNA sequence described in Example 1, and on deposit with the American Type Culture Collection, Accession Number 98169, is phosphorylated and that phosphorylation is a function of the cell cycle.

The experiments were conducted using Cell Growth Regulatory Protein in lysates prepared from human CEM cells that had been arrested at G1, S and M phases of the cell cycle by treatment with mimesine, hydroxyurea, and nocadozole, respectively. Synchronization of cells by drug block arrests was perfomed by culturing CEM cells for 16–23 hr in the presence of either 5 mM hydroxyurea (Calbiochem), 1 mM mimosine (Sigma), or 50 ng/ml nocadozole (Calbiochem). Immunoblot analysis was performed using antibody from rabbit 12390 that was injected with peptide C-47 corresponding to amino acids 472–487 (CNSEPPRGSFPSFEPRN) (Seq. ID No.14) near the C-terminus of Cell Growth Regulatory Protein. The results revealed that Cell Growth Regulatory Protein in mitotic lysates shifted to a slower migrating form. The main contribution to this modification is phosphorylation, since phosphatase treatment of the mitotic lysate decreased the migration of Cell Growth Regulatory Protein to nearly that observed in G1 and S-phase extracts. At least five laddering Cell Growth Regulatory Protein forms were detectable in the dilute phosphatase-treated mitotic lysate, indicating that multiple Cell Growth Regulatory Protein residues are phosphorylated during mitosis. Additionally, immunoblot analysis of cytosolic and detergent-extracted P100 fractions prepared from nocodazole-arrested CEM cells revealed that the phosphorylated forms of Cell Growth Regulatory Protein remained membrane-associated.

EXAMPLE 8

Assays for the Identification of Drugs to Treat Hyperproliferative Cell Growth Diseases A key aspect of the instant invention is the presentation of assays that permit the identification of unique compounds that can be used to control unwanted, or hyperproliferative cell growth. Such compounds will have significant applications for treating a variety of diseases that involve unwanted cell growth including cancer, restenosis and others known to the skilled practitioner of this art.

Two assays are described below. Both assays rely on inhibiting the activity of Cell Growth Regulatory Protein which in turn prevents the phosphorylation of cdc2/cyclinB1, which further, in turn, causes cells to progress through the cell cycle without the necessary control mechanisms. This has the effect of killing the constantly cycling cells. Thus, the assays described below measure the phosphorylation of a suitable Cell Growth Regulatory Protein substrate in the presence of test compounds to determine their effect on Cell Growth Regulatory Protein kinase activity.

1. Cdc2/CyclinB1 Histone H1 Kinase Activity

The first assay indirectly measures the kinase activity of Cell Growth Regulatory Protein. Cell Growth Regulatory Protein phosphorylates Cdc2/cyclinB1, resulting in the inactivation of the Cdc2/cyclinB1 kinase activity, as measured by the phosphorylation of histone H1. Compounds that inactivate Cell Growth Regulatory Protein kinase activity thus will cause Cdc2/cyclinB1 to retain kinase activity and can be detected by increased $^{32}$P-labeling of histone H1. Other Cdc2/cyclinB1 substrates can also be used, including GST-Rb, Cdc25, or peptides containing Cdc2 phosphorylation sites. Alternatively, other indirect measures of Cdc2/cyclinB1 activity could be incorporated into this assay, including $^{32}$P-labeling of the cyclinB1 subunit or the reduced electrophoretic mobility of Cdc2 by PAGE. Other Cdk/cyclin complexes, such as Cdc2/cyclinA or Cdc2/cyclinB2, may be used in this in-vitro Cell Growth Regulatory Protein kinase reaction. This Cell Growth Regulatory Protein assay can be performed utilizing purified Cell Growth Regulatory Protein and Cdc2/cyclinB1 proteins as well as utilizing a crude Sf9 lysate mixing format.

For example, frozen pellets of Sf9 cells expressing appropriate recombinant proteins are thawed and lysed by dounce homogenization in 10 mM Hepes, pH 7.5, 1 mM EDTA, 1% NP40, 1 mM DTT and protease inhibitors [1 mM Pefabloc, 5 mg/ml leupeptin, 5 mg/ml leupeptin] at 4° C., followed by ultracentrifugation for 30 min at 42 kpm in a TLA45 rotor at 4° C. The clarified lysates are aliquoted and stored at −80° C. Activation of Cdc2/cyclinB complexes are performed by mixing combinations of Cdc2 and cyclinB lysates, with Cell Growth Regulatory Protein lysates, together with an ATP regeneration system (10×stock: 0.5 mg/ml creatine phosphokinase, 10 mM ATP, 350 mM phosphocreatine, 1 mM, 2 mM Hepes, pH 7.5) at 25° C. for 25 min. Additionally, compounds that are tested for Cell Growth Regulatory Protein inhibitory activity are added to the reaction mixture over a range of concentrations, preferably from nanomolar to millimolar. Next, to determine the effect of a compound on Cell Growth Regulatory Protein activity by its effect on Cdc2/cyclinB kinase activity, the latter is measured using 1 ul of lysate mixture incubated with 9 ul of a histone H1 kinase mix [50 mM Tris, pH 7.5, 10 mM MgCl$_2$, 1 mM DTT, 5 ug histone H1, 50 uM ATP, 1 uCi [$^{32}$P]ATP (3000 Ci/mmol) for 10–15 min at 25° C. The amount of histone H1 phosphorylation is measured using standard polyacrylamide gel electrophoresis and autoradiography methods. The appropriate controls are run to ensure that the compounds being tested are affecting Cell Growth Regulatory Protein activity, and not interacting directly with cdc2/cyclinB.

Those compounds identified to affect Cell Growth Regulatory Protein activity will have significant prophylactic and therapeutic benefit for the treatment of hyperproliferative diseases.

2. Inhibition of Cell Growth Regulatory Protein Substrate Phosphorylation

Compounds are identified that inactivate Cell Growth Regulatory Protein kinase activity by directly measuring the phosphorylation of Cell Growth Regulatory Protein substrates, preferably Cdc2 complexed with cyclinB1. The assay is run using, as described above, lysates of the appropriate proteins, and under suitable reaction conditions including [gamma-$^{32}$P]ATP in the in-vitro kinase reaction mixture. Alternatively, phospho-specific antibodies (New England Biolabs) such as an anti-phosphothreonine antibody, may be used to detect phosphorylation of Cell Growth Regulatory Protein substrates. Additionally, the assay may be run using purified protein components.

Compounds that inhibit the kinase activity of Cell Growth Regulatory Protein will prevent the phosphorylation of cdc2/cyclinB1. Such compounds will have significant prophylactic and therapeutic benefit for the treatment of hyperproliferative diseases.

Deposit of Clones

The following microorganisms or clones were deposited with the American Type Culture Collection (ATCC), Rockville, Md., on the dates indicated and were assigned the indicated accession number:

| Clone | Access. No. | Date of Deposit |
| --- | --- | --- |
| pBSK-myt1 | 98169 | Sept. 17, 1996 |

The invention now being fully described, it will be apparent to one of ordinary skill in the art that many changes and modifications can be made thereto without departing from the spirit or scope of the appended claims.

What is claimed is:

1. An isolated nucleic acid molecule as set forth in SEQ. ID No. 1 that encodes a human Cell Growth Regulatory Protein that phosphorylates cdc2 at tyrosine 15 and threonine 14.

2. An isolated nucleic acid molecule as described in claim 1 wherein said isolated nucleic acid sequence encodes a human Cell Growth Regulatory Protein with a transmembrane region.

3. An isolated nucleic acid molecule as described in claim 2 wherein said isolated nucleic acid sequence encodes a human Cell Growth Regulatory Protein with a molecular weight of about 54.6 kd.

4. An isolated nucleic acid molecule comprising an isolated nucleic acid sequence as described in claim 3 wherein said nucleic acid sequence is a cDNA sequence.

5. An isolated nucleic acid molecule as described in claim 4 wherein said isolated nucleic acid cDNA sequence encoding said human Cell Growth Regulatory Protein comprises an isolated nucleic acid fragment of said cDNA sequence.

6. An isolated nucleic acid molecule hybridizable under high stringency conditions to said nucleic acid sequence that encodes a human Cell Growth Regulatory Protein of claim 4, said high stringency conditions comprising hybridization using 0.5 M $NaHPO_4$, 7% sodium dodecyl sulfate (SDS), 1 mM EDTA at 65° C., and washing in 0.1×SSC/0.1% SDS at 68° C.

7. Isolated host cells comprising an isolated nucleic acid molecule of claim 6 which encode a human Cell Growth Regulatory Protein.

8. Vectors that comprise an isolated nucleic acid molecule of claim 6 which encodes a human Cell Growth Regulatory Protein.

9. A plasmid on deposit with the American Type Culture Collection with accession no. 98169 which encodes a human Cell Growth Regulatory Protein.

10. Isolated host cells comprising said plasmid of claim 9 which encodes a Cell Growth Regulatory Protein.

11. A process for producing a Cell Growth Regulatory Protein comprising culturing cells of claim 7 in a suitable culture medium and isolating said protein from said cells or said medium.

* * * * *

SEQUENCE LISTING

<160> NUMBER OF SEQ ID NOS: 20

<210> SEQ ID NO 1
<211> LENGTH: 1976
<212> TYPE: DNA
<213> ORGANISM: Human Myt1
<220> FEATURE:
<221> NAME/KEY: CDS
<222> LOCATION: Complement((327)..(1823))
<223> OTHER INFORMATION: Human Myt1

<400> SEQUENCE: 1

| | | |
|---|---|---|
| caggactccc gtgaggggga acggcccgtg aacgcgcgcg agctgctcg cgccccgccc | 60 | |
| agtcgcccca gggcttcccc acacccacgg agtgaagtca gccgcggccc tgcctgggag | 120 | |
| gaacttaccg tctaccggga aagtggcca gcagatgtgt cgggcctggt gagagggtga | 180 | |
| ggcgagacgg cccgatcgcc cagggccccg gaagctgcgg aggtcacccc cgcctggcct | 240 | |
| tagctcaggg acaccctgga ttcacgtggg agccctgct cctgcctccc ccgtcccacc | 300 | |
| actgaagctg ttgggccagg ccagtc atg cta gaa cgg cct cct gca ctg gcc | 353 | |

```
                           Met Leu Glu Arg Pro Pro Ala Leu Ala
                             1               5 atg ccc atg ccc acg gag ggc acc ccg cca cct ctg agt ggc acc ccc   401
Met Pro Met Pro Thr Glu Gly Thr Pro Pro Pro Leu Ser Gly Thr Pro
 10                  15                  20                  25 atc cca gtc cca gcc tac ttc cgc cac gca gaa cct gga ttc tcc ctc   449
Ile Pro Val Pro Ala Tyr Phe Arg His Ala Glu Pro Gly Phe Ser Leu
                 30                  35                  40 aag agg ccc agg ggg ctc agc cgg agc ctc cca cct ccg ccc cct gcc   497
Lys Arg Pro Arg Gly Leu Ser Arg Ser Leu Pro Pro Pro Pro Pro Ala
             45                  50                  55 aag ggc agc att ccc atc agc cgc ctc ttc cct cct cgg acc cca ggc   545
Lys Gly Ser Ile Pro Ile Ser Arg Leu Phe Pro Pro Arg Thr Pro Gly
         60                  65                  70 tgg cac cag ctg cag ccc cgg cgg gtg tca ttc cgg ggc gag gcc tca   593
Trp His Gln Leu Gln Pro Arg Arg Val Ser Phe Arg Gly Glu Ala Ser
     75                  80                  85 gag act ctg cag agc cct ggg tat gac cca agc cgg cca gag tcc ttc   641
Glu Thr Leu Gln Ser Pro Gly Tyr Asp Pro Ser Arg Pro Glu Ser Phe
 90                  95                 100                 105 ttc cag cag agc ttc cag agg ctc agc cgc ctg ggc cat ggc tcc tac   689
Phe Gln Gln Ser Phe Gln Arg Leu Ser Arg Leu Gly His Gly Ser Tyr
                110                 115                 120 gga gag gtc ttc aag gtg cgc tcc aag gag gac ggc cgg ctc tat gcg   737
Gly Glu Val Phe Lys Val Arg Ser Lys Glu Asp Gly Arg Leu Tyr Ala
            125                 130                 135 gta aag cgt tcc atg tca cca ttc cgg ggc ccc aag gac cgg gcc cgc   785
Val Lys Arg Ser Met Ser Pro Phe Arg Gly Pro Lys Asp Arg Ala Arg
        140                 145                 150 aag ttg gcc gag gtg ggc agc cac gag aag gtg ggg cag cac cca tgc   833
Lys Leu Ala Glu Val Gly Ser His Glu Lys Val Gly Gln His Pro Cys
    155                 160                 165 tgc gtg cgg ctg gag cag gcc tgg gag gag ggc ggc atc ctg tac ctg   881
Cys Val Arg Leu Glu Gln Ala Trp Glu Glu Gly Gly Ile Leu Tyr Leu
170                 175                 180                 185 cag acg gag ctg tgc ggg ccc agc ctg cag caa cac tgt gaa gcc tgg   929
Gln Thr Glu Leu Cys Gly Pro Ser Leu Gln Gln His Cys Glu Ala Trp
                190                 195                 200
```

-continued

```
ggt gcc agc ctg cct gag gcc cag gtc tgg ggc tac ctg cgg gac acg      977
Gly Ala Ser Leu Pro Glu Ala Gln Val Trp Gly Tyr Leu Arg Asp Thr
            205                 210                 215 ctg ctt gcc ctg gcc cat ctg cac agc cag ggc ctg gtg cac ctt gat     1025
Leu Leu Ala Leu Ala His Leu His Ser Gln Gly Leu Val His Leu Asp
            220                 225                 230 gtc aag cct gcc aac atc ttc ctg ggg ccc cgg ggc cgc tgc aag ctg     1073
Val Lys Pro Ala Asn Ile Phe Leu Gly Pro Arg Gly Arg Cys Lys Leu
        235                 240                 245 ggt gac ttc gga ctg ctg gtg gag ctg ggt aca gca gga gct ggt gag     1121
Gly Asp Phe Gly Leu Leu Val Glu Leu Gly Thr Ala Gly Ala Gly Glu
250                 255                 260                 265 gtc cag gag gga gac ccc cgc tac atg gcc ccc gag ctg ctg cag ggc     1169
Val Gln Glu Gly Asp Pro Arg Tyr Met Ala Pro Glu Leu Leu Gln Gly
            270                 275                 280 tcc tat ggg aca gca gcg gat gtg ttc agt ctg ggc ctc acc atc ctg     1217
Ser Tyr Gly Thr Ala Ala Asp Val Phe Ser Leu Gly Leu Thr Ile Leu
            285                 290                 295 gaa gtg gca tgc aac atg gag ctg ccc cac ggt ggg gag ggc tgg cag     1265
Glu Val Ala Cys Asn Met Glu Leu Pro His Gly Gly Glu Gly Trp Gln
        300                 305                 310 cag ctg cgc cag ggc tac ctg ccc cct gag ttc act gcc ggt ctg tct     1313
Gln Leu Arg Gln Gly Tyr Leu Pro Pro Glu Phe Thr Ala Gly Leu Ser
        315                 320                 325 tcc gag ctg cgt tct gtc ctt gtc atg atg ctg gag cca gac ccc aag     1361
Ser Glu Leu Arg Ser Val Leu Val Met Met Leu Glu Pro Asp Pro Lys
330                 335                 340                 345 ctg cgg gcc acg gcc gag gcc ctg ctg gca ctg cct gtg ttg agg cag     1409
Leu Arg Ala Thr Ala Glu Ala Leu Leu Ala Leu Pro Val Leu Arg Gln
            350                 355                 360 ccg cgg gcc tgg ggt gtg ctg tgg tgc atg gca gcg gag gcc ctg agc     1457
Pro Arg Ala Trp Gly Val Leu Trp Cys Met Ala Ala Glu Ala Leu Ser
            365                 370                 375 cga ggg tgg gcc ctg tgg cag gcc ctg ctt gcc ctg ctc tgc tgg ctc     1505
Arg Gly Trp Ala Leu Trp Gln Ala Leu Leu Ala Leu Leu Cys Trp Leu
        380                 385                 390 tgg cat ggg ctg gct cac cct gcc agc tgg cta cag ccc ctg ggc ccg     1553
Trp His Gly Leu Ala His Pro Ala Ser Trp Leu Gln Pro Leu Gly Pro
        395                 400                 405 cca gcc acc ccg cct gac tca cca ccc tgc agt ttg ctc ctg gac agc     1601
Pro Ala Thr Pro Pro Asp Ser Pro Pro Cys Ser Leu Leu Leu Asp Ser
410                 415                 420                 425 agc ttc tcc agc aac tgg gat gac gac agc cta ggg cct tca ctc tcc     1649
Ser Phe Ser Ser Asn Trp Asp Asp Asp Ser Leu Gly Pro Ser Leu Ser
            430                 435                 440 cct gag gct gtc ctg gcc cgg act gtg ggg agc acc tcc acc ccc cgg     1697
Pro Glu Ala Val Leu Ala Arg Thr Val Gly Ser Thr Ser Thr Pro Arg
            445                 450                 455 agc agg tgc aca ccc agg gat gcc ctg gac cta agt gac atc aac tca     1745
Ser Arg Cys Thr Pro Arg Asp Ala Leu Asp Leu Ser Asp Ile Asn Ser
        460                 465                 470 gag cct cct cgg ggc tcc ttc ccc tcc ttt gag cct cgg aac ctc ctc     1793
Glu Pro Pro Arg Gly Ser Phe Pro Ser Phe Glu Pro Arg Asn Leu Leu
        475                 480                 485 agc atg ttt gag gac acc cta gac cca acc tgagcccag attctgcctc        1843
Ser Met Phe Glu Asp Thr Leu Asp Pro Thr
490                 495 tgcactttta acctttatc ctgtgtctct cccgtcgccc ttgaaagctg gggcccctcg    1903
```

-continued

```
ggaactccca tggtcttctc tgcctggccg tgtctaataa aaagtatttg aaccttgaaa    1963
aaaaaaaaag aag                                                      1976
```

<210> SEQ ID NO 2
<211> LENGTH: 499
<212> TYPE: PRT
<213> ORGANISM: Human Myt1

<400> SEQUENCE: 2

```
Met Leu Glu Arg Pro Pro Ala Leu Ala Met Pro Met Pro Thr Glu Gly
  1               5                  10                  15

Thr Pro Pro Leu Ser Gly Thr Pro Ile Pro Val Pro Ala Tyr Phe
                 20                  25                  30

Arg His Ala Glu Pro Gly Phe Ser Leu Lys Arg Pro Arg Gly Leu Ser
                 35                  40                  45

Arg Ser Leu Pro Pro Pro Pro Ala Lys Gly Ser Ile Pro Ile Ser
             50                  55                  60

Arg Leu Phe Pro Pro Arg Thr Pro Gly Trp His Gln Leu Gln Pro Arg
 65                  70                  75                  80

Arg Val Ser Phe Arg Gly Glu Ala Ser Glu Thr Leu Gln Ser Pro Gly
                 85                  90                  95

Tyr Asp Pro Ser Arg Pro Glu Ser Phe Gln Gln Ser Phe Gln Arg
                100                 105                 110

Leu Ser Arg Leu Gly His Gly Ser Tyr Gly Glu Val Phe Lys Val Arg
            115                 120                 125

Ser Lys Glu Asp Gly Arg Leu Tyr Ala Val Lys Arg Ser Met Ser Pro
        130                 135                 140

Phe Arg Gly Pro Lys Asp Arg Ala Arg Lys Leu Ala Glu Val Gly Ser
145                 150                 155                 160

His Glu Lys Val Gly Gln His Pro Cys Cys Val Arg Leu Glu Gln Ala
                165                 170                 175

Trp Glu Glu Gly Gly Ile Leu Tyr Leu Gln Thr Glu Leu Cys Gly Pro
            180                 185                 190

Ser Leu Gln Gln His Cys Glu Ala Trp Gly Ala Ser Leu Pro Glu Ala
        195                 200                 205

Gln Val Trp Gly Tyr Leu Arg Asp Thr Leu Leu Ala Leu Ala His Leu
    210                 215                 220

His Ser Gln Gly Leu Val His Leu Asp Val Lys Pro Ala Asn Ile Phe
225                 230                 235                 240

Leu Gly Pro Arg Gly Arg Cys Lys Leu Gly Asp Phe Gly Leu Leu Val
                245                 250                 255

Glu Leu Gly Thr Ala Gly Ala Gly Glu Val Gln Glu Gly Asp Pro Arg
            260                 265                 270

Tyr Met Ala Pro Glu Leu Leu Gln Gly Ser Tyr Gly Thr Ala Ala Asp
        275                 280                 285

Val Phe Ser Leu Gly Leu Thr Ile Leu Glu Val Ala Cys Asn Met Glu
    290                 295                 300

Leu Pro His Gly Gly Glu Gly Trp Gln Gln Leu Arg Gln Gly Tyr Leu
305                 310                 315                 320

Pro Pro Glu Phe Thr Ala Gly Leu Ser Ser Glu Leu Arg Ser Val Leu
                325                 330                 335

Val Met Met Leu Glu Pro Asp Pro Lys Leu Arg Ala Thr Ala Glu Ala
            340                 345                 350
```

-continued

```
Leu Leu Ala Leu Pro Val Leu Arg Gln Pro Arg Ala Trp Gly Val Leu
        355                 360                 365
Trp Cys Met Ala Ala Glu Ala Leu Ser Arg Gly Trp Ala Leu Trp Gln
370                 375                 380
Ala Leu Ala Leu Leu Cys Trp Leu Trp His Gly Leu Ala His Pro
385                 390                 395                 400
Ala Ser Trp Leu Gln Pro Leu Gly Pro Pro Ala Thr Pro Pro Asp Ser
                405                 410                 415
Pro Pro Cys Ser Leu Leu Leu Asp Ser Ser Phe Ser Ser Asn Trp Asp
            420                 425                 430
Asp Asp Ser Leu Gly Pro Ser Leu Ser Pro Glu Ala Val Leu Ala Arg
        435                 440                 445
Thr Val Gly Ser Thr Ser Thr Pro Arg Ser Arg Cys Thr Pro Arg Asp
    450                 455                 460
Ala Leu Asp Leu Ser Asp Ile Asn Ser Glu Pro Pro Arg Gly Ser Phe
465                 470                 475                 480
Pro Ser Phe Glu Pro Arg Asn Leu Leu Ser Met Phe Glu Asp Thr Leu
                485                 490                 495
Asp Pro Thr

<210> SEQ ID NO 3
<211> LENGTH: 21
<212> TYPE: DNA
<213> ORGANISM: Oligonucleotide

<400> SEQUENCE: 3
agcagcctct ccagcaactg g                                           21

<210> SEQ ID NO 4
<211> LENGTH: 21
<212> TYPE: DNA
<213> ORGANISM: Oligonucleotide

<400> SEQUENCE: 4
cagagaagac catggagttc c                                           21

<210> SEQ ID NO 5
<211> LENGTH: 23
<212> TYPE: DNA
<213> ORGANISM: Oligonucleotide

<400> SEQUENCE: 5
tcgaattcat gcccatgccc acg                                         23

<210> SEQ ID NO 6
<211> LENGTH: 12
<212> TYPE: PRT
<213> ORGANISM: Glu Tagged Truncated Myt1

<400> SEQUENCE: 6

Met Glu Tyr Met Pro Met Glu Gly Thr Arg Pro Glu
  1               5                  10

<210> SEQ ID NO 7
<211> LENGTH: 23
<212> TYPE: PRT
<213> ORGANISM: Glu Tagged Truncated Wee1

<400> SEQUENCE: 7
```

-continued

Met Glu Tyr Met Pro Met Glu Gly Thr Arg Pro Glu Phe Glu Leu Gly
 1               5                  10                  15

Thr Arg Gly Ser Asp Trp Ser
            20

<210> SEQ ID NO 8
<211> LENGTH: 17
<212> TYPE: PRT
<213> ORGANISM: Glu Tagged Truncated Wee1

<400> SEQUENCE: 8

Met Glu Tyr Met Pro Met Glu Glu Val Pro Gly Leu Asn Ser Ala Trp
 1               5                  10                  15

Ser

<210> SEQ ID NO 9
<211> LENGTH: 12
<212> TYPE: PRT
<213> ORGANISM: Glu Tagged CDC2

<400> SEQUENCE: 9

Thr Met Glu Tyr Met Pro Met Glu Gly Tyr Gln Ala
 1               5                  10

<210> SEQ ID NO 10
<211> LENGTH: 12
<212> TYPE: PRT
<213> ORGANISM: Glu Tagged CDK2

<400> SEQUENCE: 10

Ser Met Glu Tyr Met Pro Met Glu Gly Tyr Gln Ala
 1               5                  10

<210> SEQ ID NO 11
<211> LENGTH: 20
<212> TYPE: PRT
<213> ORGANISM: Glu Tagged Cyclin A

<400> SEQUENCE: 11

Met Glu Tyr Met Pro Met Glu Glu Val Pro Gly Leu Asn Ser Cys Ser
 1               5                  10                  15

Pro Gly Ala Val
            20

<210> SEQ ID NO 12
<211> LENGTH: 20
<212> TYPE: PRT
<213> ORGANISM: Glu Tagged Cyclin D

<400> SEQUENCE: 12

Met Glu Tyr Met Pro Met Glu Glu Val Pro Gly Leu Asn Ser Cys Arg
 1               5                  10                  15

Ala Arg Ile Ser
            20

<210> SEQ ID NO 13
<211> LENGTH: 21
<212> TYPE: PRT
<213> ORGANISM: Glu Tagged Cyclin E

<400> SEQUENCE: 13

Met Glu Tyr Met Pro Met Glu Gly Thr Arg Pro Glu Phe Arg Asp Ala
 1               5                  10                  15

Lys Glu Arg Asp Thr
            20

<210> SEQ ID NO 14
<211> LENGTH: 17
<212> TYPE: PRT
<213> ORGANISM: Myt1 Peptide C-47

<400> SEQUENCE: 14

Cys Asn Ser Glu Pro Pro Arg Gly Ser Phe Pro Ser Phe Glu Pro Arg
 1               5                  10                  15

Asn

<210> SEQ ID NO 15
<211> LENGTH: 15
<212> TYPE: PRT
<213> ORGANISM: Myt1 Peptide C-49

<400> SEQUENCE: 15

Cys Arg Asn Leu Leu Ser Met Phe Glu Asp Thr Leu Asp Pro Thr
 1               5                  10                  15

<210> SEQ ID NO 16
<211> LENGTH: 15
<212> TYPE: PRT
<213> ORGANISM: Myt1 Peptide C-48

<400> SEQUENCE: 16

Met Pro Met Pro Thr Glu Gly Thr Pro Pro Leu Ser Gly Cys
 1               5                  10                  15

<210> SEQ ID NO 17
<211> LENGTH: 23
<212> TYPE: DNA
<213> ORGANISM: Oligonucleotide

<400> SEQUENCE: 17
tcggatccat gcccatgccc acg                                        23

<210> SEQ ID NO 18
<211> LENGTH: 104
<212> TYPE: DNA
<213> ORGANISM: pAcO-G1

<400> SEQUENCE: 18
aagatctcca tggaatacat gccaatggaa ggtactaggc ctgaattcct gcagagctcg    60
gatcctctag agctagcggc cgcccgggcc gtaccgactc tgct                    104

<210> SEQ ID NO 19
<211> LENGTH: 105
<212> TYPE: DNA
<213> ORGANISM: pAcO-G2

<400> SEQUENCE: 19
aagatctcca tggaatacat gccaatggaa gggtaccagg cctgaattcc tgcagagctc    60
ggatcctcta gagctagcgg ccgcccgggc cgtaccgact ctgct                   105

<210> SEQ ID NO 20
<211> LENGTH: 106
<212> TYPE: DNA
<213> ORGANISM: pAcO-G3

-continued

```
<400> SEQUENCE: 20
aagatctcca tggaatacat gccaatggaa gaggtaccag gcctgaattc ctgcagagct      60
cggatcctct agagctagcg gccgcccggg ccgtaccgac tctgct                   106
```